US008709748B2

(12) United States Patent
Walsh et al.

(10) Patent No.: US 8,709,748 B2
(45) Date of Patent: *Apr. 29, 2014

(54) METHOD FOR DETECTION AND CHARACTERIZATION OF A MICROORGANISM IN A SAMPLE USING TIME-DEPENDENT INTRINSIC FLUORESCENCE MEASUREMENTS

(71) Applicant: bioMerieux, Inc., Durham, NC (US)

(72) Inventors: John Walsh, Durham, NC (US); Jones Hyman, Wake Forest, NC (US); Bradford Clay, Wildwood, MO (US); Thurman Thorpe, Durham, NC (US)

(73) Assignee: bioMerieux, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/928,857

(22) Filed: Jun. 27, 2013

(65) Prior Publication Data

US 2013/0288295 A1   Oct. 31, 2013

Related U.S. Application Data

(63) Continuation of application No. 12/460,607, filed on Jul. 22, 2009, now Pat. No. 8,512,975.

(60) Provisional application No. 61/135,839, filed on Jul. 24, 2008.

(51) Int. Cl.
*C12Q 1/04* (2006.01)

(52) U.S. Cl.
USPC ........................................ 435/34; 435/288.7

(58) Field of Classification Search
USPC ................................................ 435/34, 288.7
See application file for complete search history.

(56) References Cited

U.S. PATENT DOCUMENTS

| 4,577,110 | A | 3/1986 | MacBride et al. |
| 5,164,796 | A | 11/1992 | Di Guiseppi et al. |
| 5,217,875 | A | 6/1993 | Karpf et al. |
| 5,266,486 | A | 11/1993 | Fraatz et al. |
| 5,474,910 | A | 12/1995 | Alfano |
| 5,770,454 | A | 6/1998 | Essenpreis et al. |
| 5,938,617 | A | 8/1999 | Vo-Dinh |
| 6,074,870 | A | 6/2000 | Berndt et al. |
| 6,087,182 | A | 7/2000 | Jeng et al. |
| 6,124,597 | A | 9/2000 | Shehada et al. |
| 6,346,421 | B1 | 2/2002 | Anderson et al. |
| 6,718,077 | B1 | 4/2004 | Ferreira et al. |
| 6,788,394 | B1 | 9/2004 | Garcia-Rubio et al. |
| 6,794,659 | B2 | 9/2004 | Barbieri et al. |
| 6,834,237 | B2 | 12/2004 | Noergaard et al. |
| 7,027,134 | B1 | 4/2006 | Garcia-Rubio et al. |
| 7,070,739 | B1 | 7/2006 | Anderson et al. |
| 7,186,990 | B2 | 3/2007 | Powers et al. |
| 7,211,377 | B1 | 5/2007 | Powers et al. |
| 7,824,883 | B2 * | 11/2010 | Powers et al. ............... 435/34 |
| 8,512,975 | B2 * | 8/2013 | Walsh et al. ................ 435/34 |
| 2003/0138906 | A1 | 7/2003 | Tryland et al. |
| 2004/0197927 | A1 | 10/2004 | Jeng et al. |
| 2005/0070020 | A1 | 3/2005 | Klautky et al. |
| 2007/0111225 | A1 | 5/2007 | Lambert et al. |
| 2007/0175278 | A1 | 8/2007 | Puppels et al. |
| 2008/0032327 | A1 | 2/2008 | Powers et al. |
| 2008/0259313 | A1 | 10/2008 | Berndt |
| 2009/0306932 | A1 | 12/2009 | Li et al. |
| 2010/0068755 | A1 * | 3/2010 | Walsh et al. ................ 435/34 |
| 2010/0120085 | A1 * | 5/2010 | Hyman et al. .............. 435/34 |
| 2010/0124763 | A1 * | 5/2010 | Walsh et al. ................ 435/34 |
| 2010/0129814 | A1 * | 5/2010 | Walsh et al. ................. 435/6 |
| 2010/0129857 | A1 * | 5/2010 | Walsh et al. ................ 435/34 |
| 2010/0129858 | A1 * | 5/2010 | Walsh et al. ................ 435/34 |
| 2010/0136609 | A1 * | 6/2010 | Clay et al. .................. 435/34 |
| 2010/0291619 | A1 * | 11/2010 | Robinson et al. .......... 435/34 |
| 2011/0033847 | A1 * | 2/2011 | Walsh et al. ................. 435/6 |
| 2012/0135454 | A1 * | 5/2012 | Walsh et al. ................ 435/34 |
| 2012/0276578 | A1 * | 11/2012 | Stringari et al. ............ 435/34 |

FOREIGN PATENT DOCUMENTS

| WO | WO 2002/21108 | 3/2002 |
| WO | WO 2007/019462 | 2/2007 |
| WO | WO 2007/030020 | 3/2007 |
| WO | WO 2009/011585 | 1/2009 |
| WO | WO 2009/049171 | 4/2009 |
| WO | WO 2009/100197 | 8/2009 |
| WO | WO 2009/120532 | 10/2009 |

OTHER PUBLICATIONS

Alimova et al., "Native Fluorescence Changes Induced by Bactericidal Agents." IEEE Sensors Journal, vol. 5, No. 4, (2005) 704-711.
Pau et al., "A Rapid Enzymatic Procedure for "Fingerprinting" Bacteria by Using Pattern Recognition of Two-Dimensional Fluorescence Data", Clin. Chem., 32/6, (1986) 987-991.
Pau et al., "Evaluation of a Fourier-Transform-Based Pattern-Recognition Algorithm for Two-Dimensional Fluorescence Data", App. Spectroscopy, vol. 41, No. 3, (1987) 496-502.
Rativa et al., "Optical Spectroscopy on in vitro Fungal Diagnosis", Conf. Proc. IEEE Eng. Med. Biol. Soc., vol. 1, (2008) 4871-4874.
Roselle et al., "Changes in intrinsic fluorescence during the production of viable but nonculturable *Escherichia coli*", J. Ind. Micro. & Biotech, 20, (1998) 265-267.
Shelly et al., "Identification of Fluorescent Pseudomonas Species", Clin. Chem., 26/8, (1980) 1127-1132.
Shelly et al., "Characterization of Bacteria by Mixed-Dye Fluorometry", Clin. Chem., 29/2, (1983) 290-296.
Sorrell et al., "Bacterial Identification of Otitis Media With Fluorescence Spectroscopy", Lasers in Surgery and Medicine, vol. 14, (1994) 155-163.
Spector et al., "Noninvasive Fluorescence Identification of Bacteria Causing Acute Otitis Media in a Chinchilla Model", Laryngoscope, vol. 110, (2000) 1119-1123.
Warner et al., "Multicomponent Analysis in Clinical Chemistry by Use of Rapid Scanning Fluorescence Spectroscopy", Clin. Chem., 22/9, (1976) 1483-1492.

(Continued)

*Primary Examiner* — Ralph Gitomer

(57) ABSTRACT

The present invention provides a method for detecting, and characterizing a microorganism present in a sample and growth composition whereby the method may be accomplished utilizing a time-dependent spectroscopic technique to obtain at least two measurements directly from a sample and growth composition and correlating said measurements for the detection and characterization of a microorganism, that may be present in the sample.

18 Claims, 37 Drawing Sheets

(56) References Cited

OTHER PUBLICATIONS

International Search Report and the Written Opinion of the International Searching Authority for PCT/US2009/051473, dated May 10, 2010.

Co-pending U.S. Appl. No. 12/589,929, "Methods for the Isolation and Identification of Microorganisms" filed Oct. 30, 2009.

Ammor MS, "Recent Advances in the use of Intrinsic Fluorescence for Bacterial Identification and Characterization", J. Fluoresc., vol. 17, (2007) 455-459.

Bhatta et al., "Use of Fluorescence Spectroscopy to Differentiate Yeast and Bacterial Cells" Appl. Microbiol. Biotechnol., vol. 71, (2006) 121-126.

Bronk et al., "Variability of Steady-State Bacterial Fluorescence with Respect to Growth Conditions" App. Spectroscopy, vol. 47, No. 4, (1993) 436-440.

Cleary et al., "Intrinsic optical properties of bacterial spores and cells", Mol. Cell.And Tissue Eng., Proc. of the IEEE-EMBS Sp. Top. Conf., Piscataway, NJ (2002) 139-140.

Dalterio et al., "Steady-State and Decay Characteristics of Protein Tryptophan Fluorescence from Bacteria", App. Spectroscopy, vol. 40, No. 1, (1986) 86-90.

Dalterio et al., "The Steady-State and Decay Characteristics of Primary Fluorescence From Live Bacteria", App. Spectroscopy, vol. 41, No. 2, (1987) 234-241.

Estes et al., "Reagentless Detection of Microorganisms by Intrinsic Fluorescence", Biosens. Bioelectron., vol. 18, No. 5-6, (2003) 511-519.

Giana et al., "Rapid Identification of Bacterial Species by Fluorescence Spectroscopy and Classification Through Principal Component Analysis", J. Fluoresc., vol. 13, (2003) 489-493.

Ginell et al., "Fluorescent Spectrophotometry in the Identification of Bacteria", J. Appl. Bact., 35(1), (1972) 29-36.

Leblanc et al., "Monitoring the identity of bacteria using their intrinsic fluorescence", FEMS Microbiology Letters 211, (2002)147-153.

Mason et al., "Taxonomic Identification of Microorganisms by Capture and Intrinsic Fluorescence Detection", Biosens. Bioelectron., vol. 18, No. 5-6, (2003) 521-527.

Co-pending U.S. Appl. No. 12/589,952, "Methods for Separation, Characterization and/or Identification of Microorganisms Using Spectrometry" filed Oct. 30, 2009.

Co-pending U.S. Appl. No. 12/589,968, "Methods for Detection, Characterization and/or Identification of Microorganisms in a Sealed Container" filed Oct. 30, 2009.

Co-pending U.S. Appl. No. 12/589,976, "Methods for the Separation, Characterization and/or Identification of Microorganisms Using Raman Spectroscopy" filed Oct. 30, 2009.

Co-pending U.S. Appl. No. 12/589,985, "Methods for Separation and Characterization of Microorganisms Using Identifier Agents" filed Oct. 30, 2009.

* cited by examiner

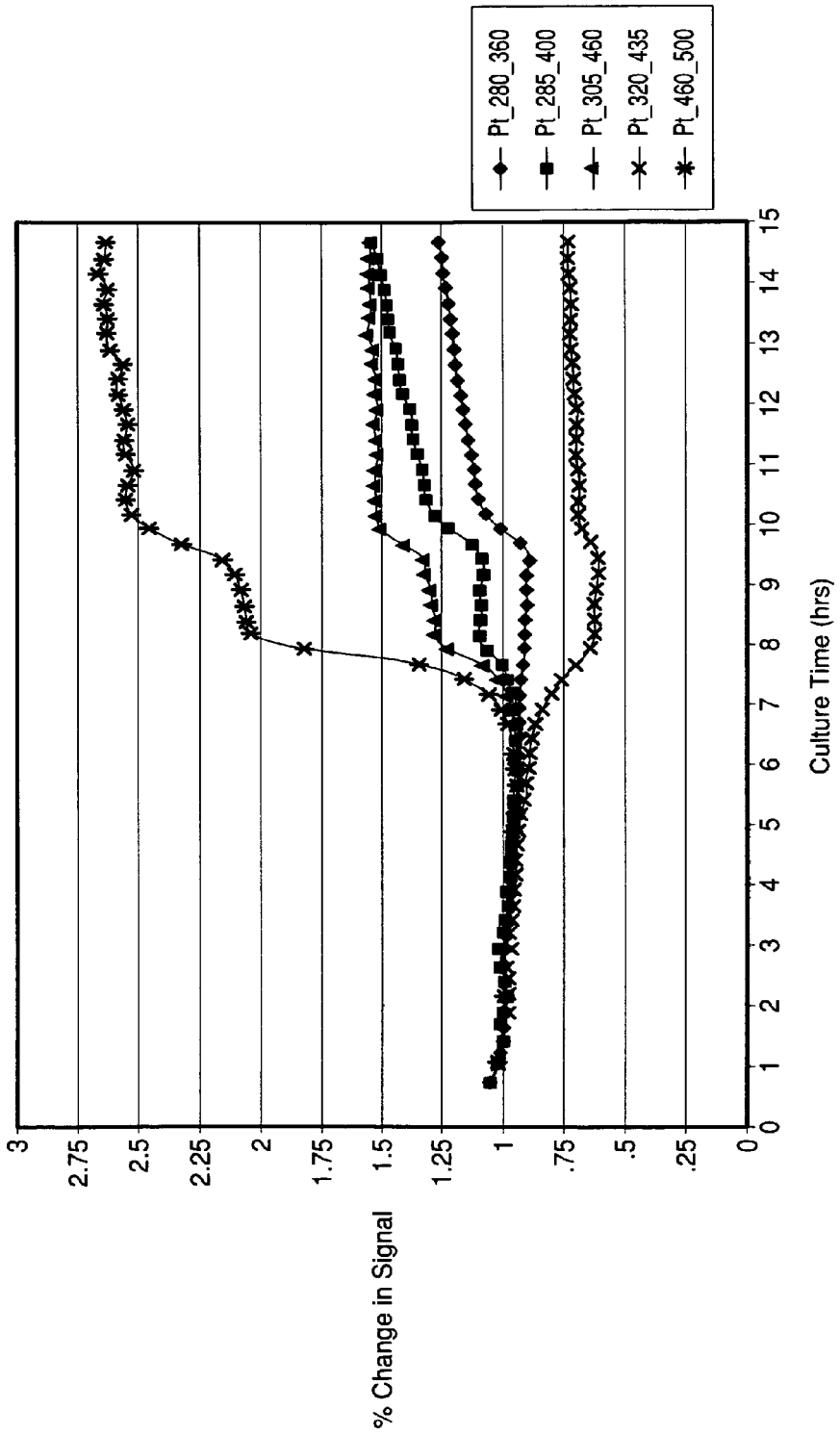

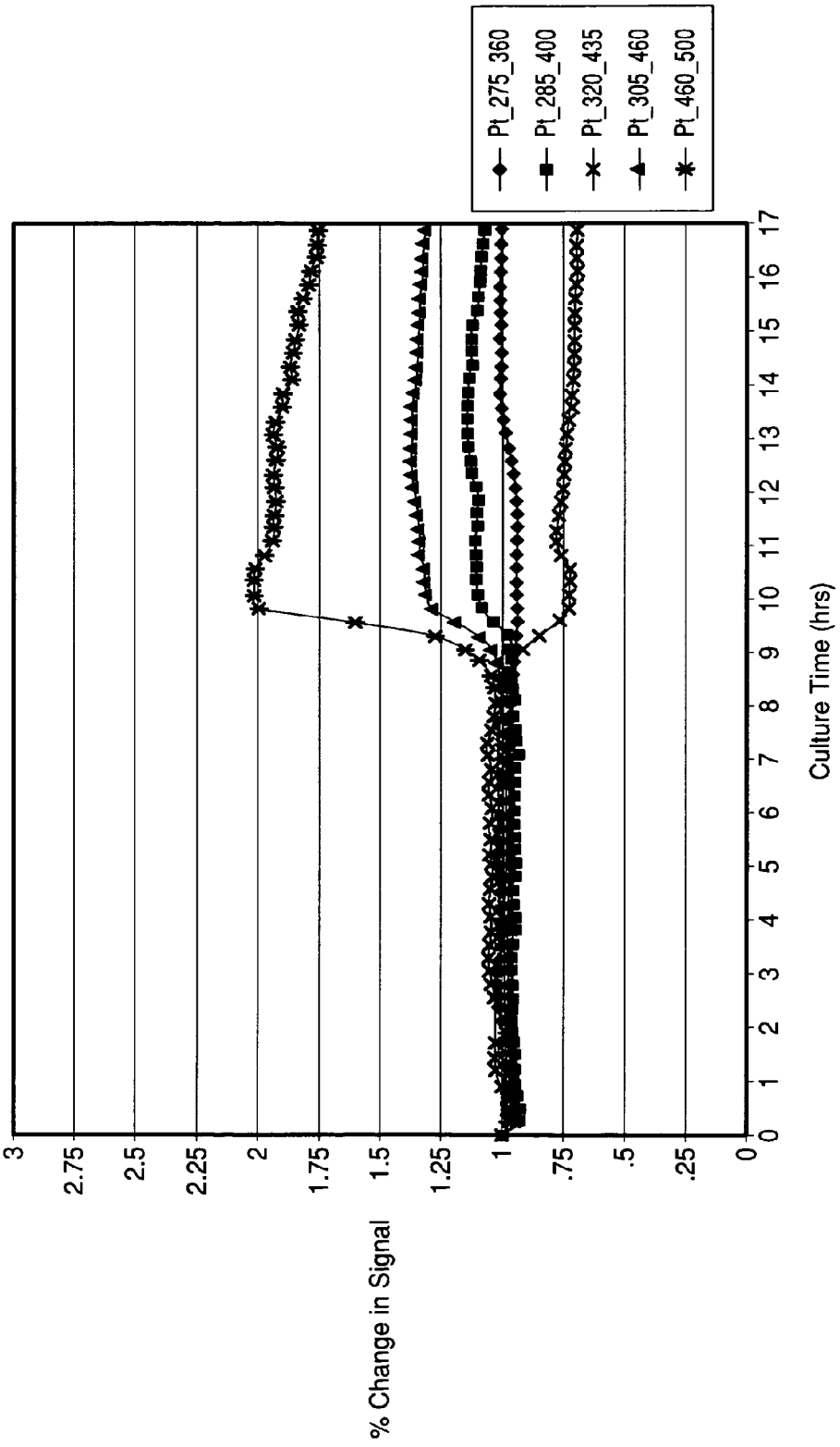

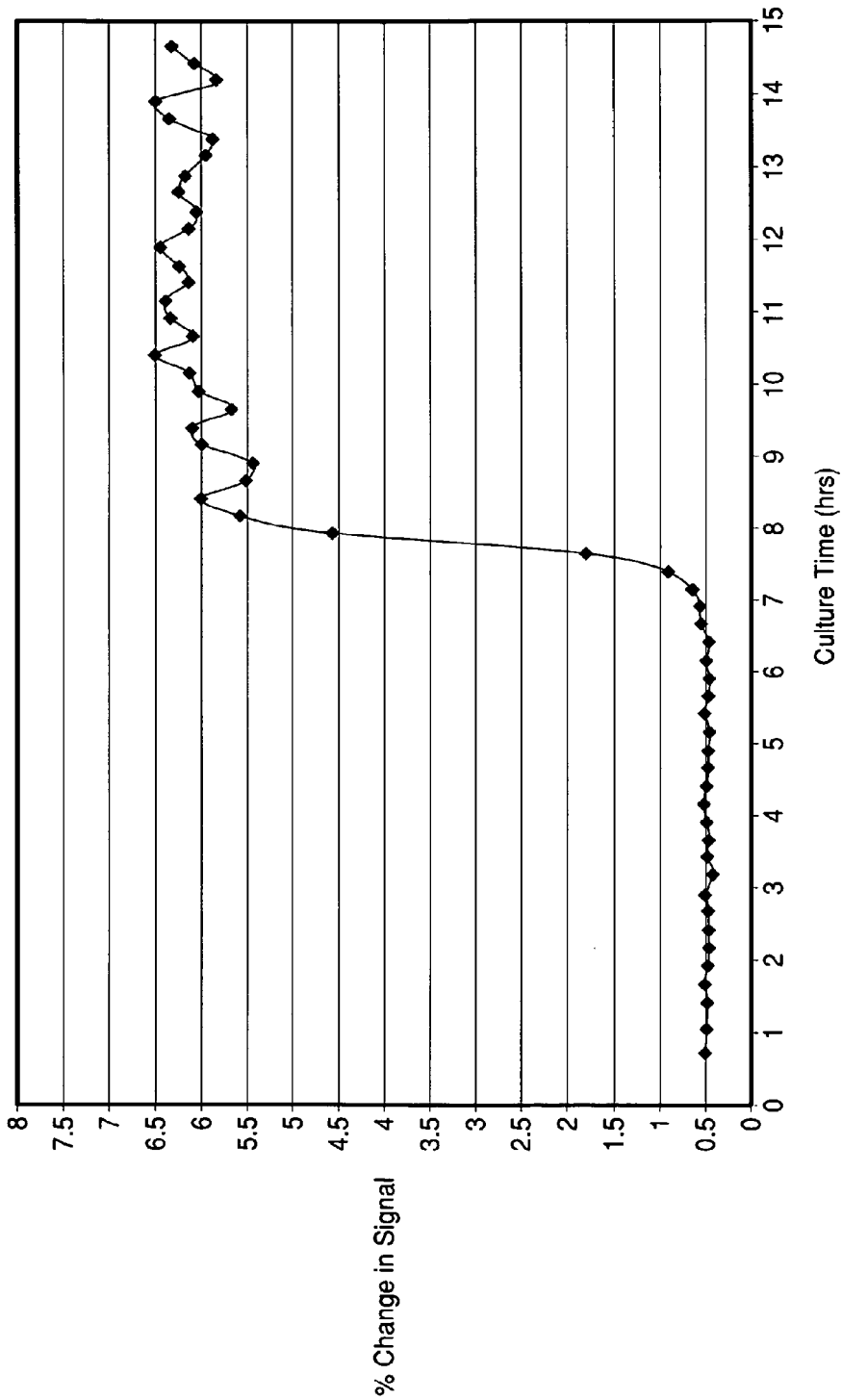

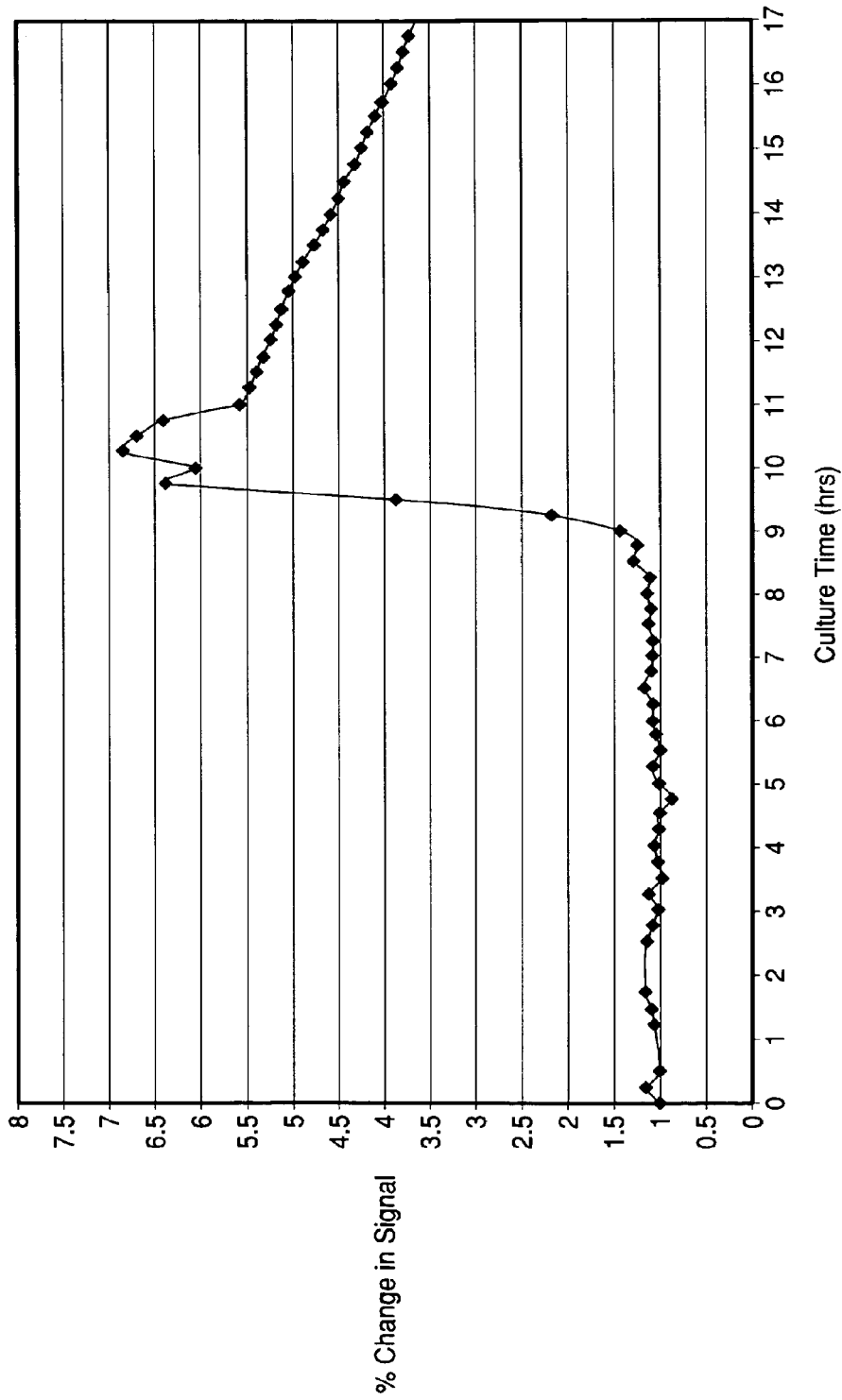

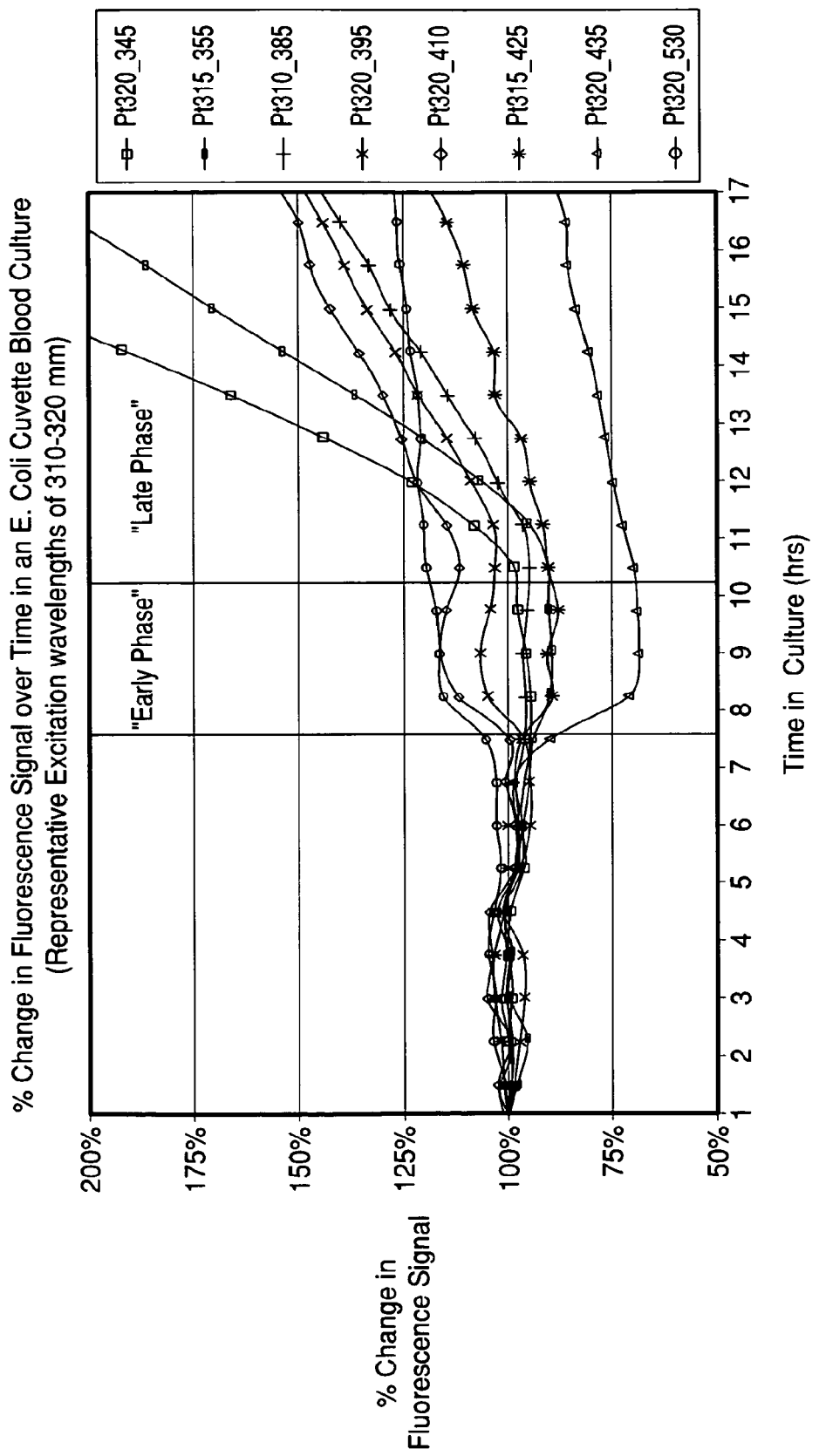

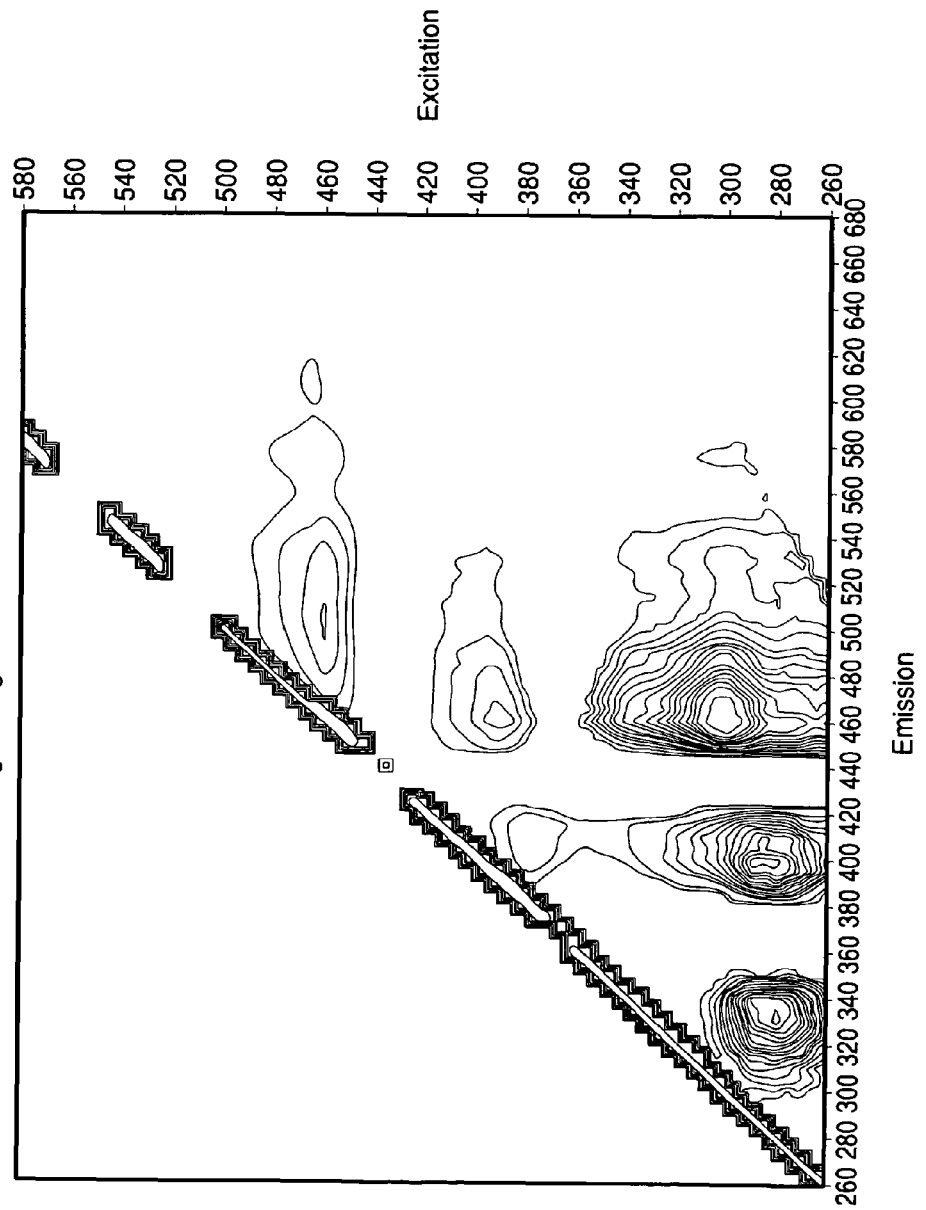

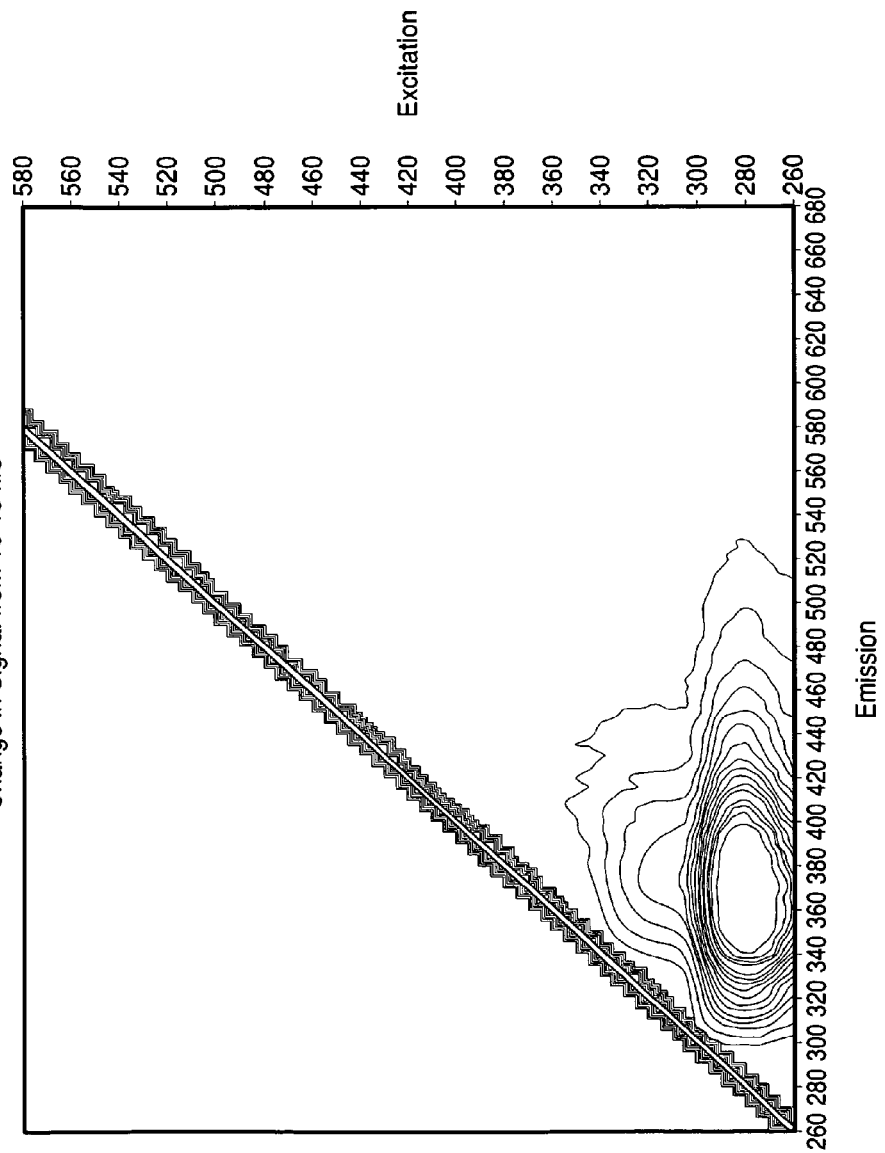

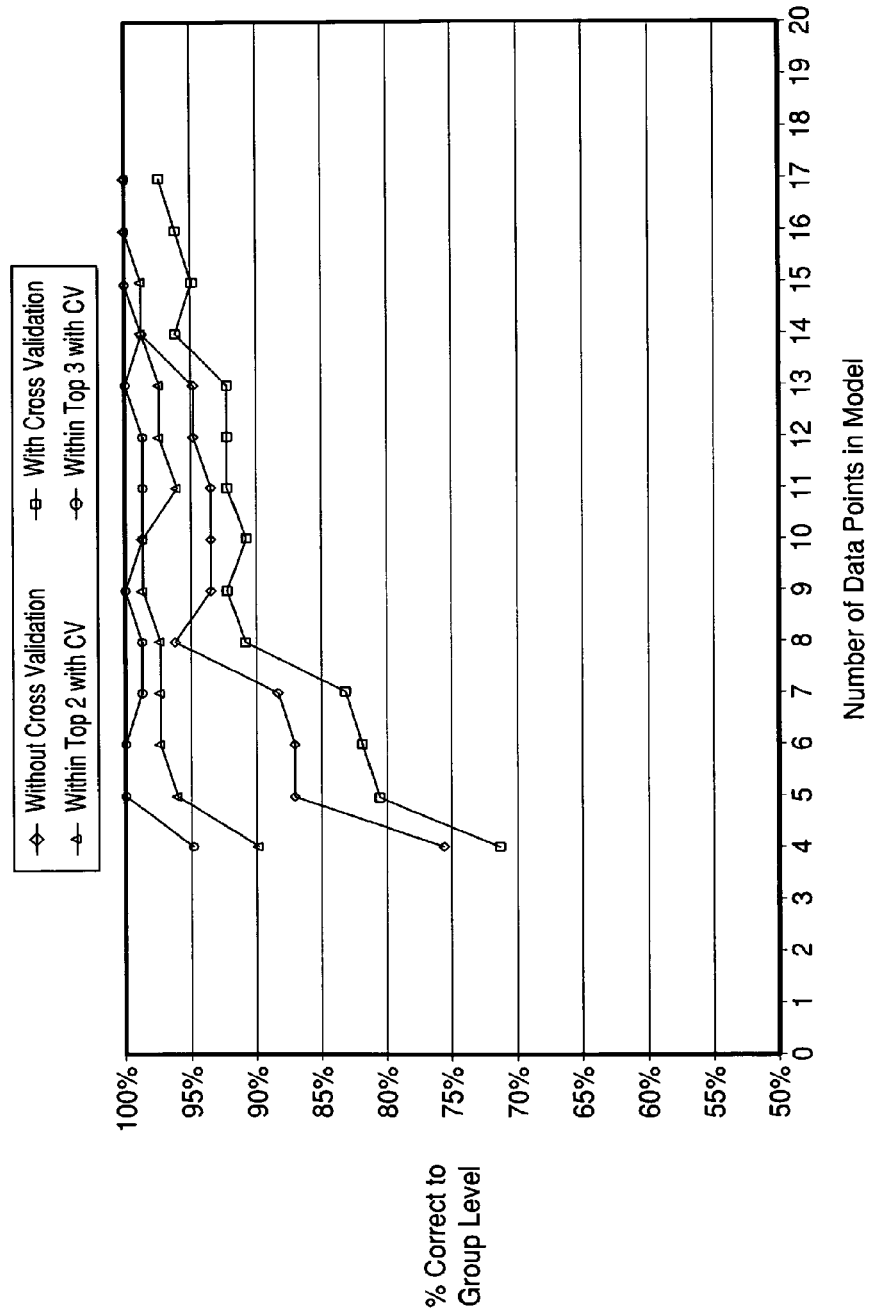

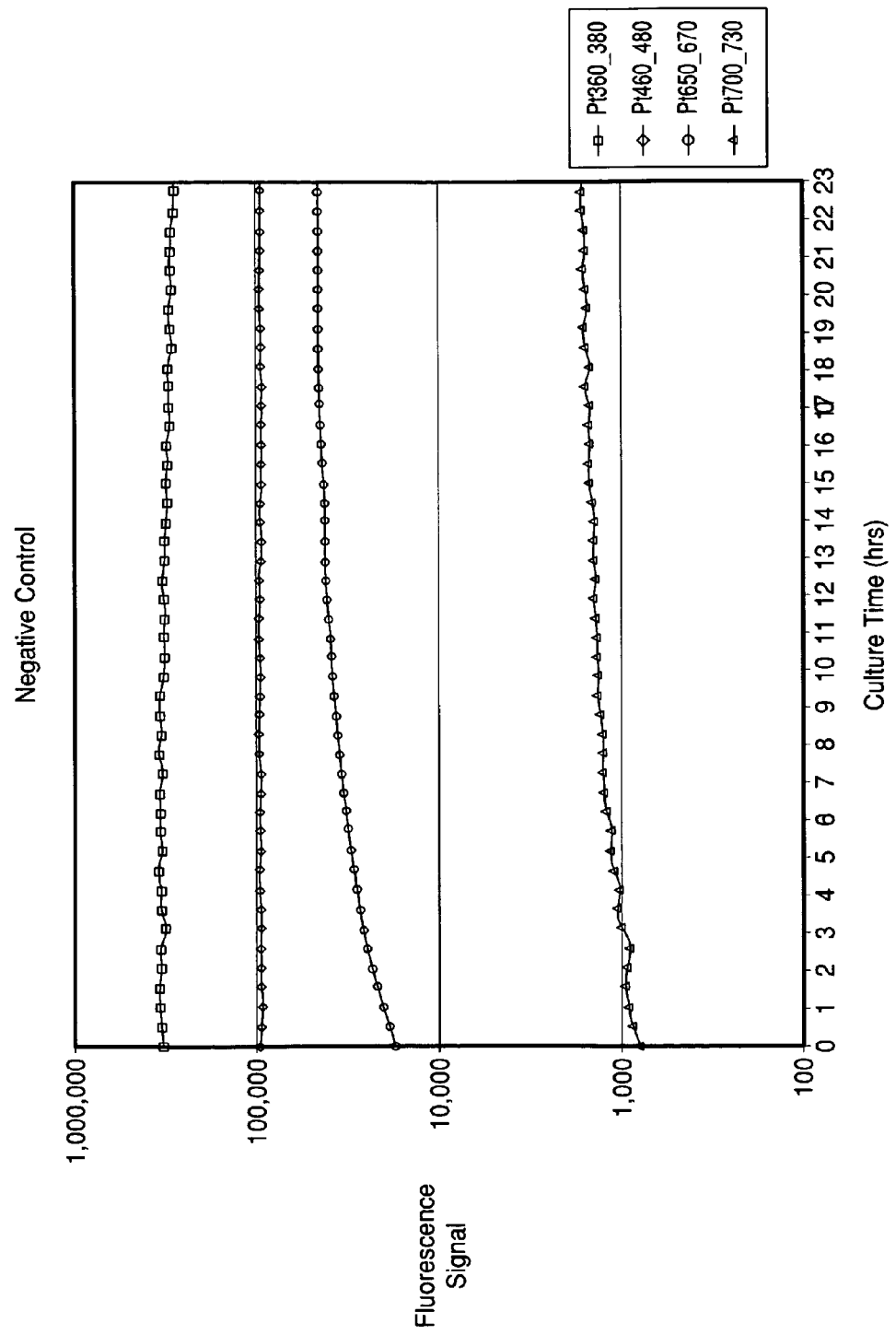

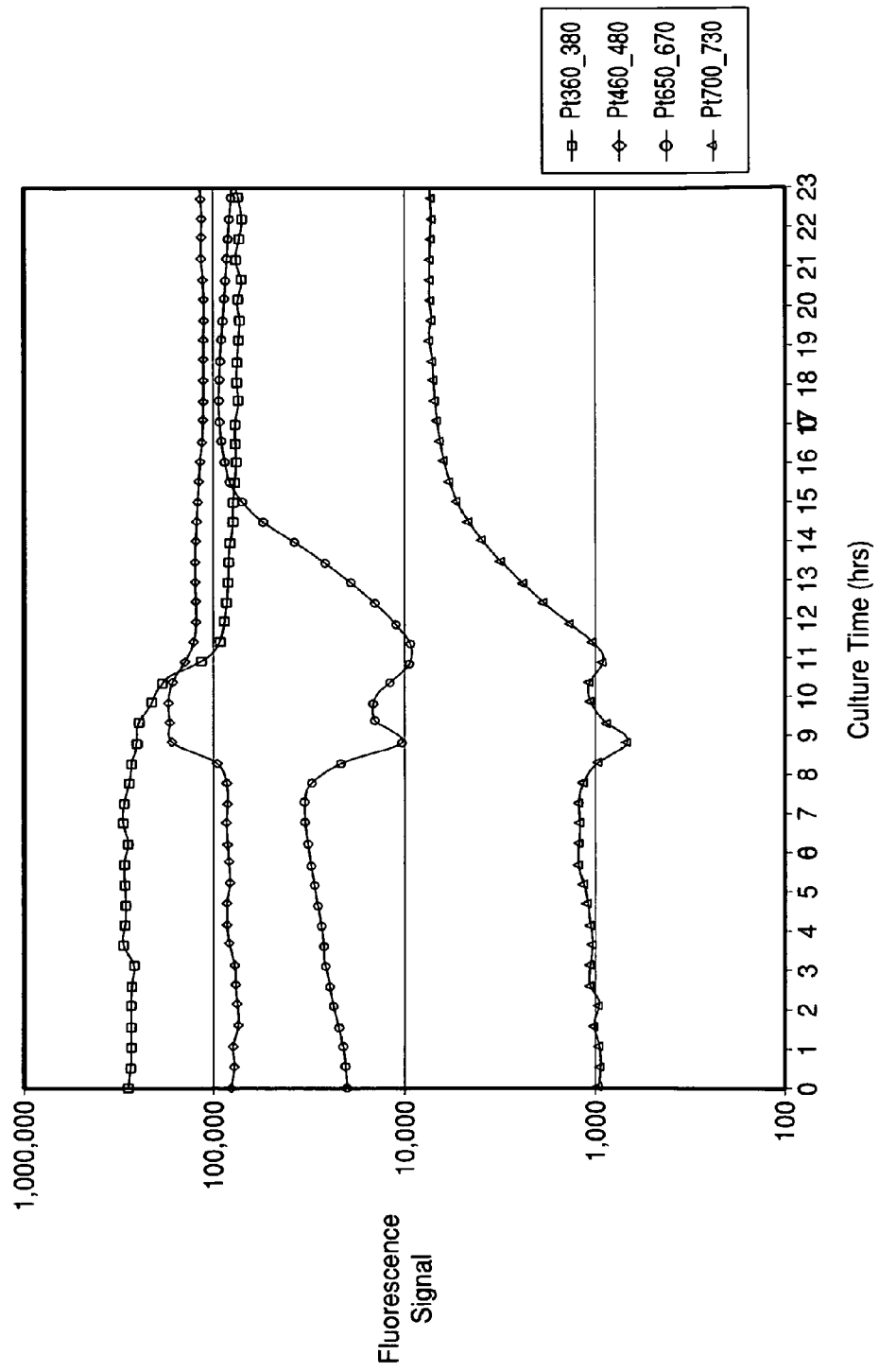

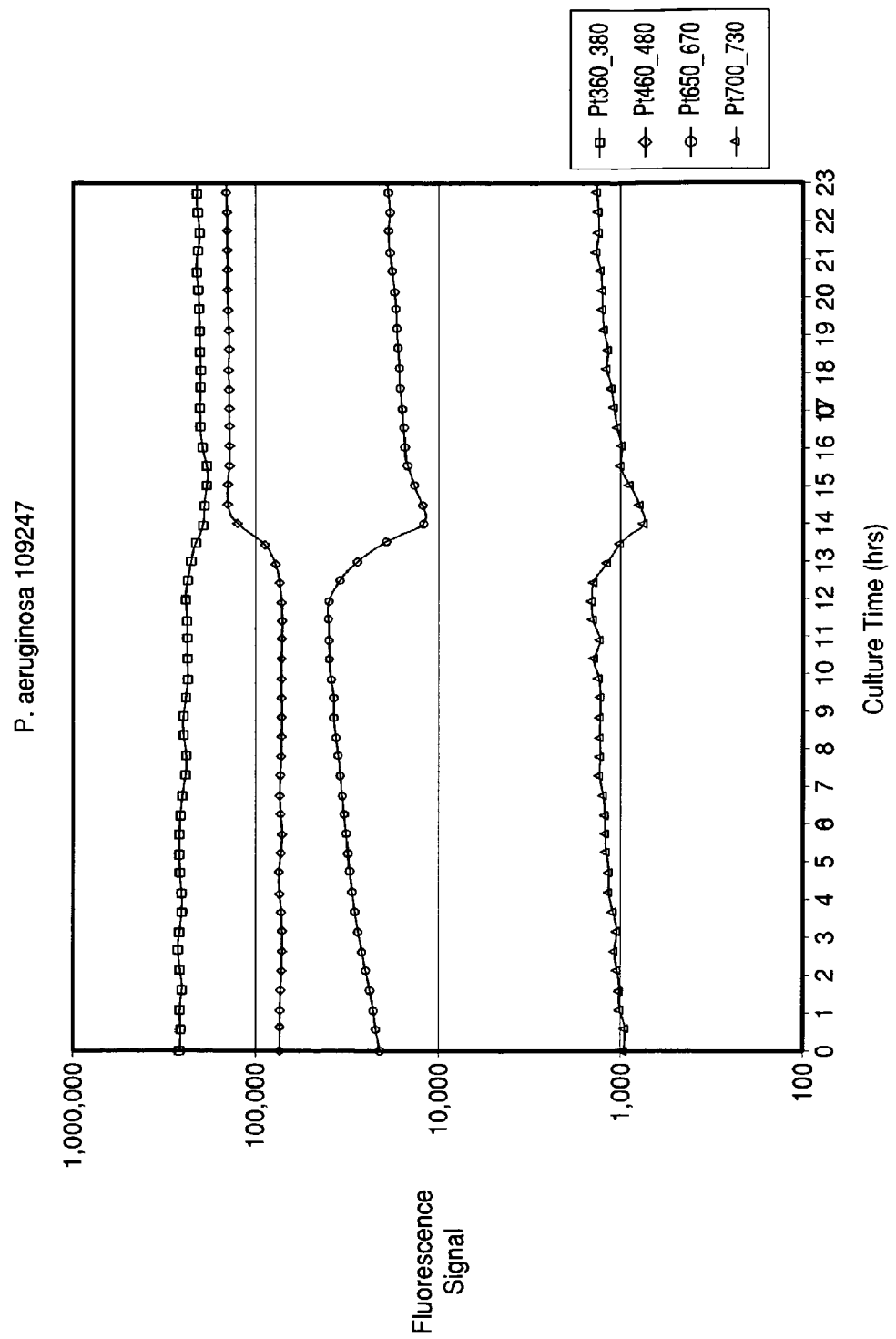

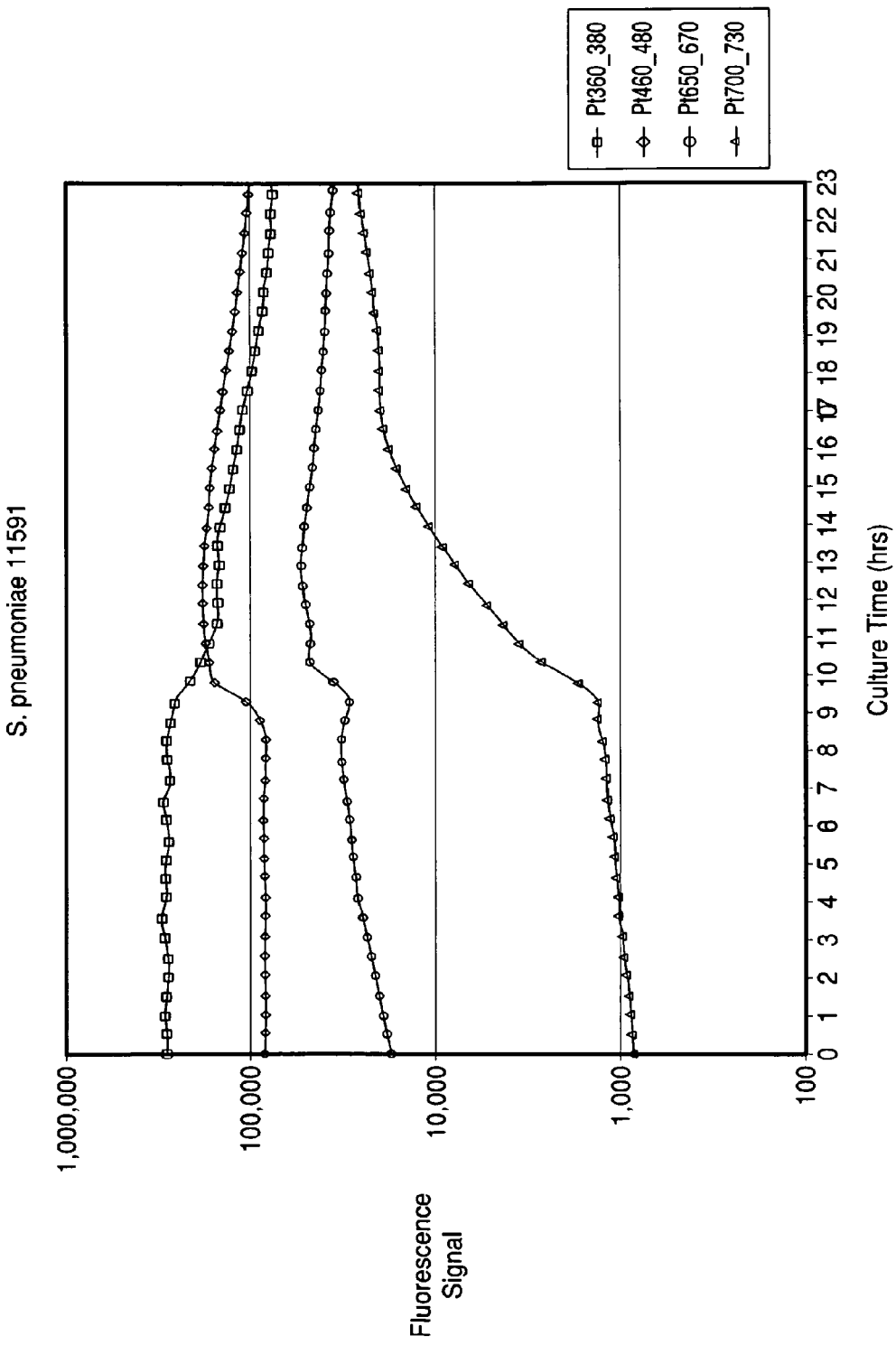

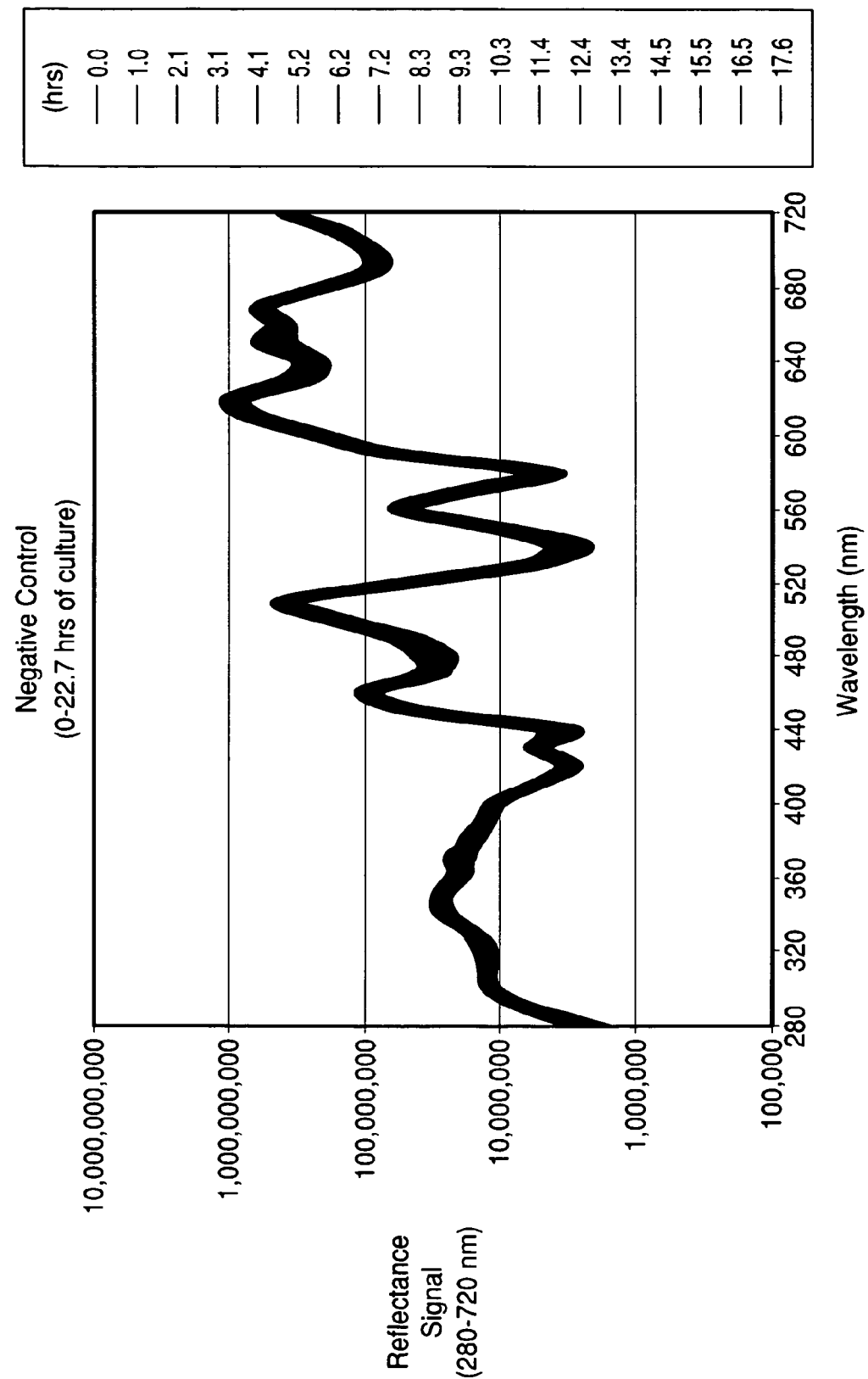

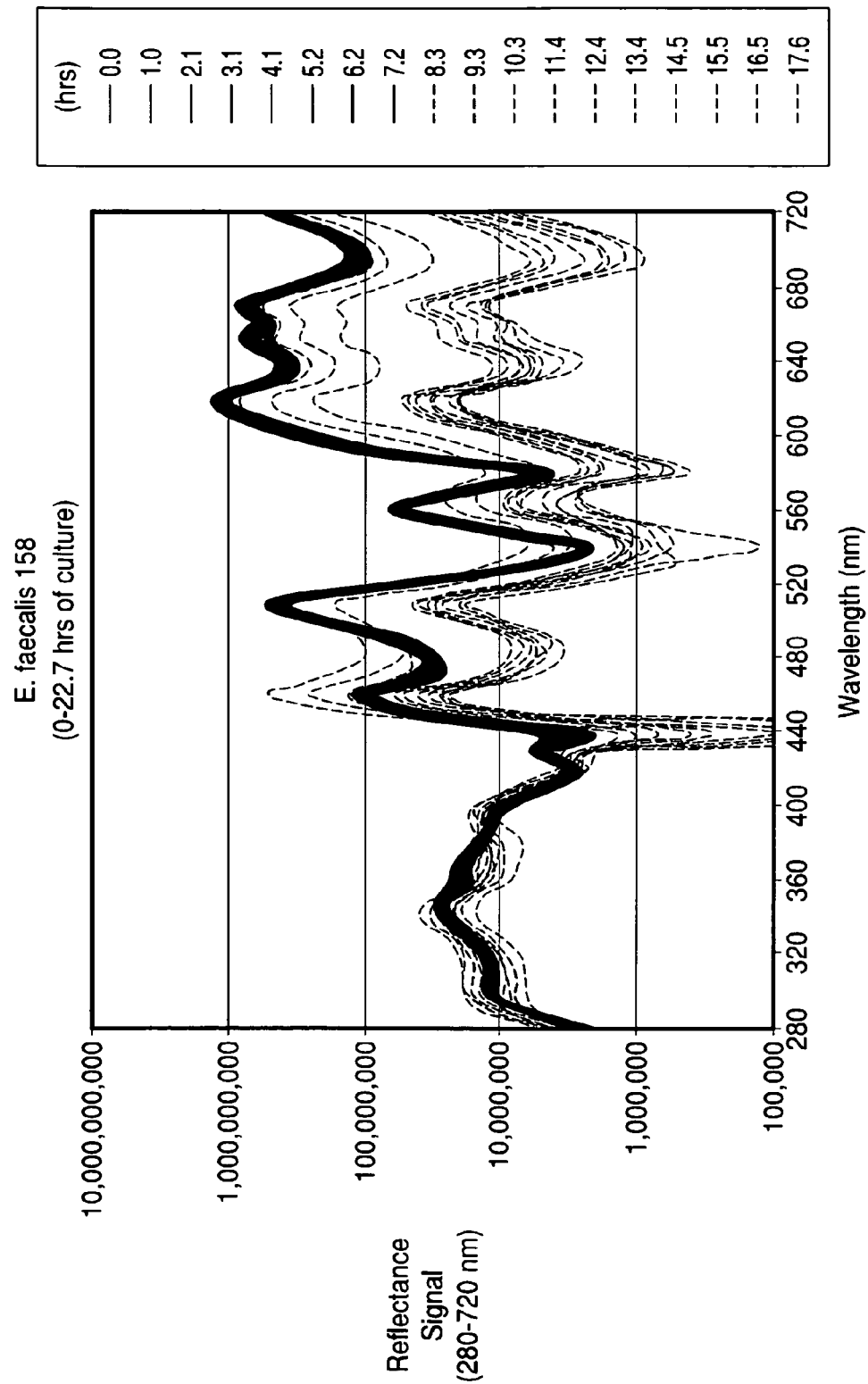

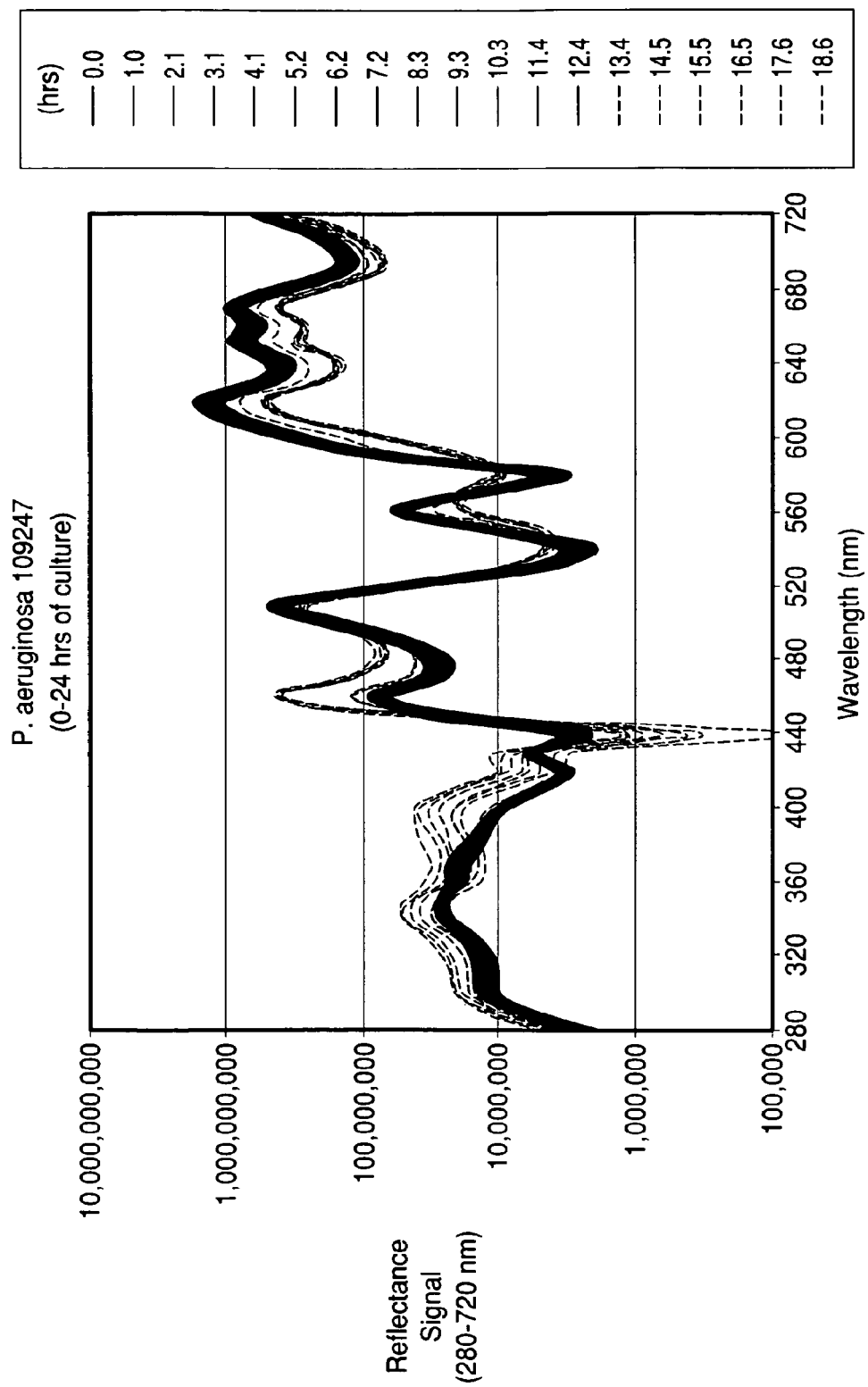

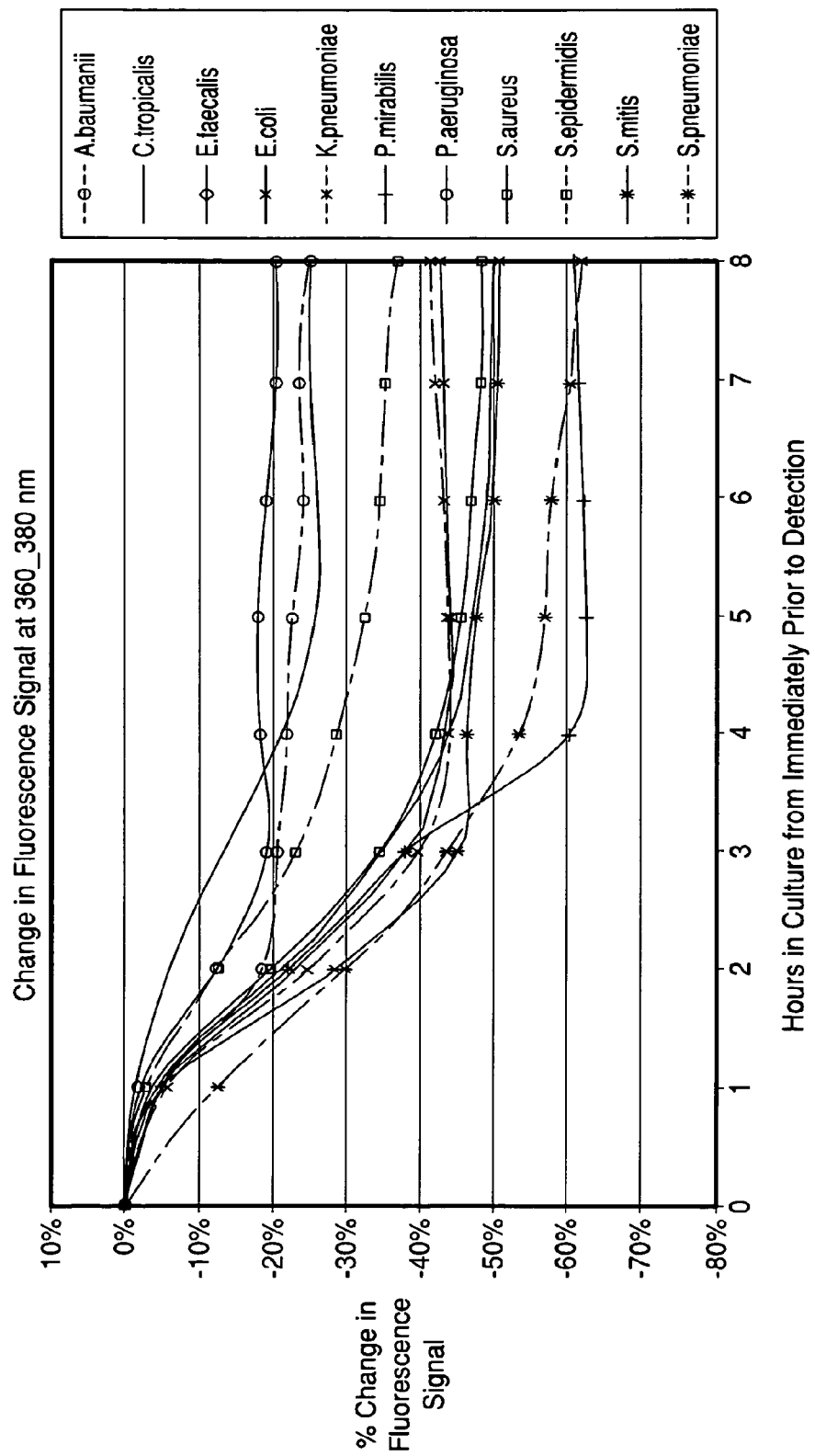

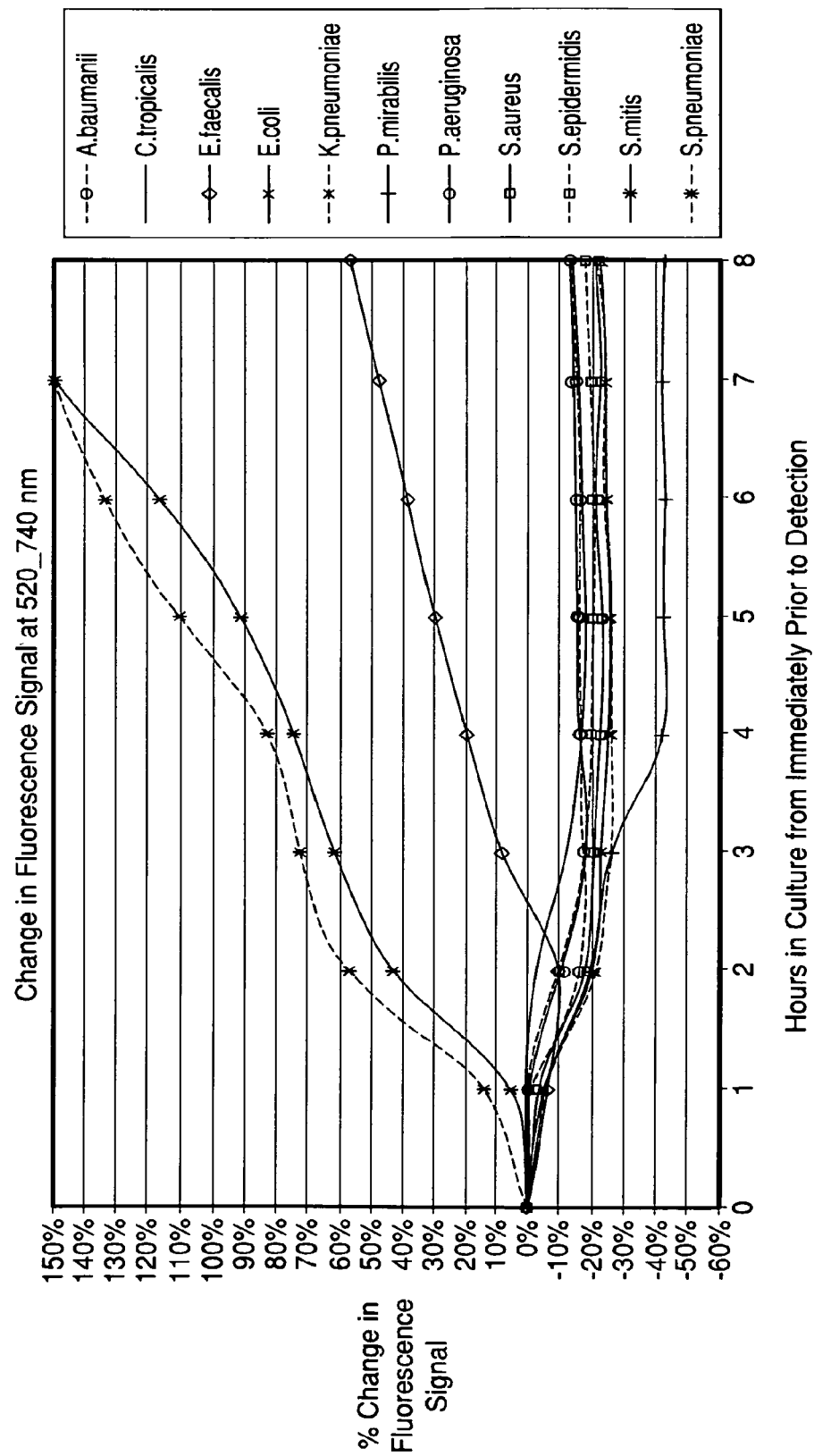

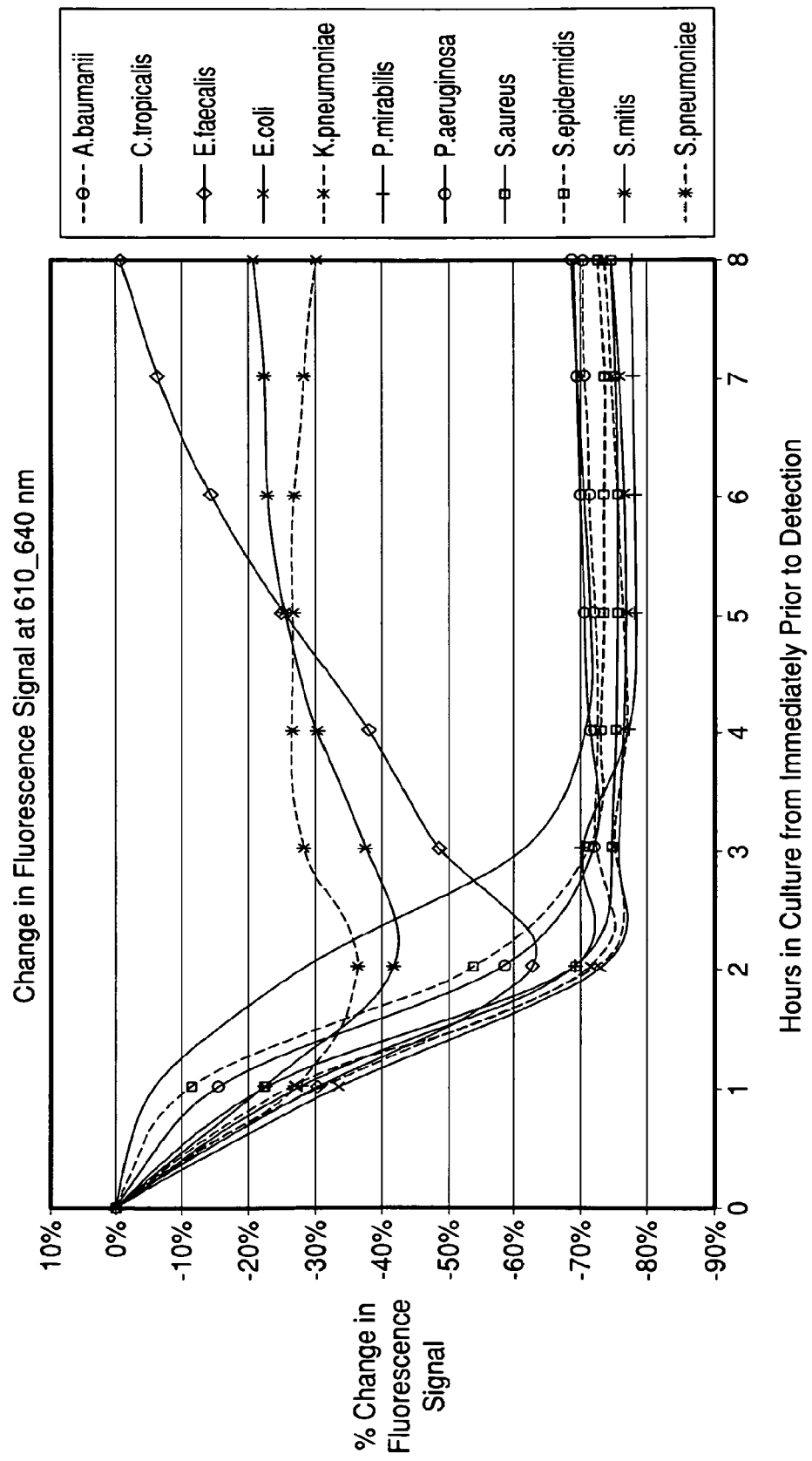

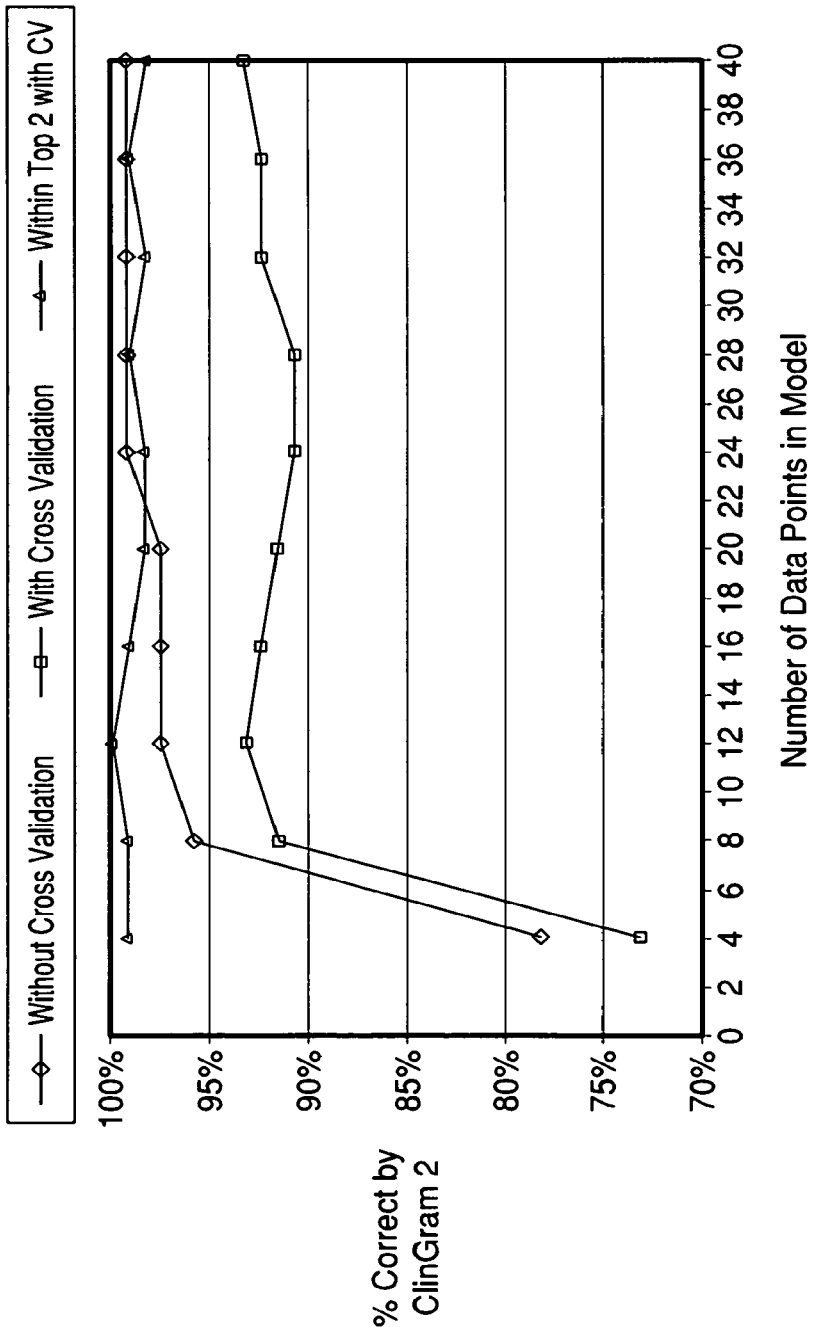

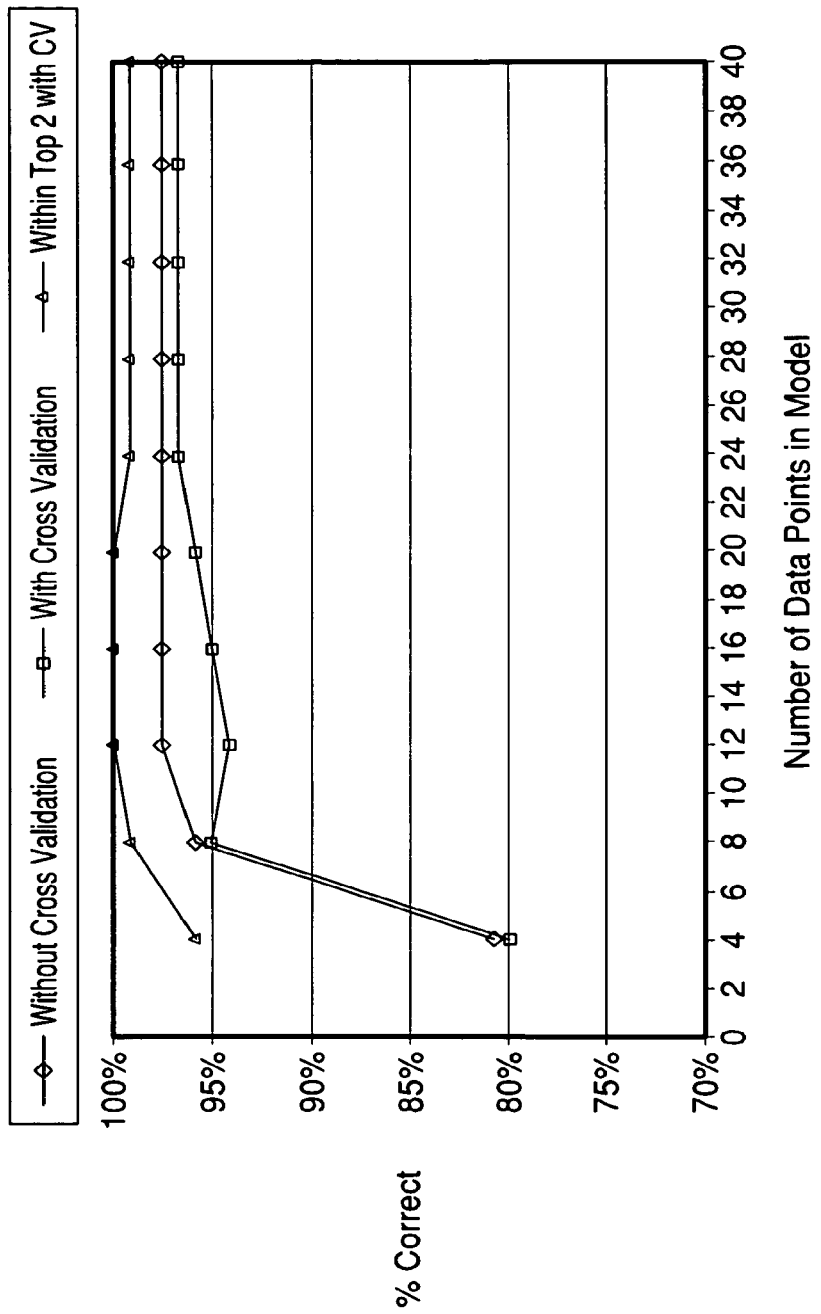

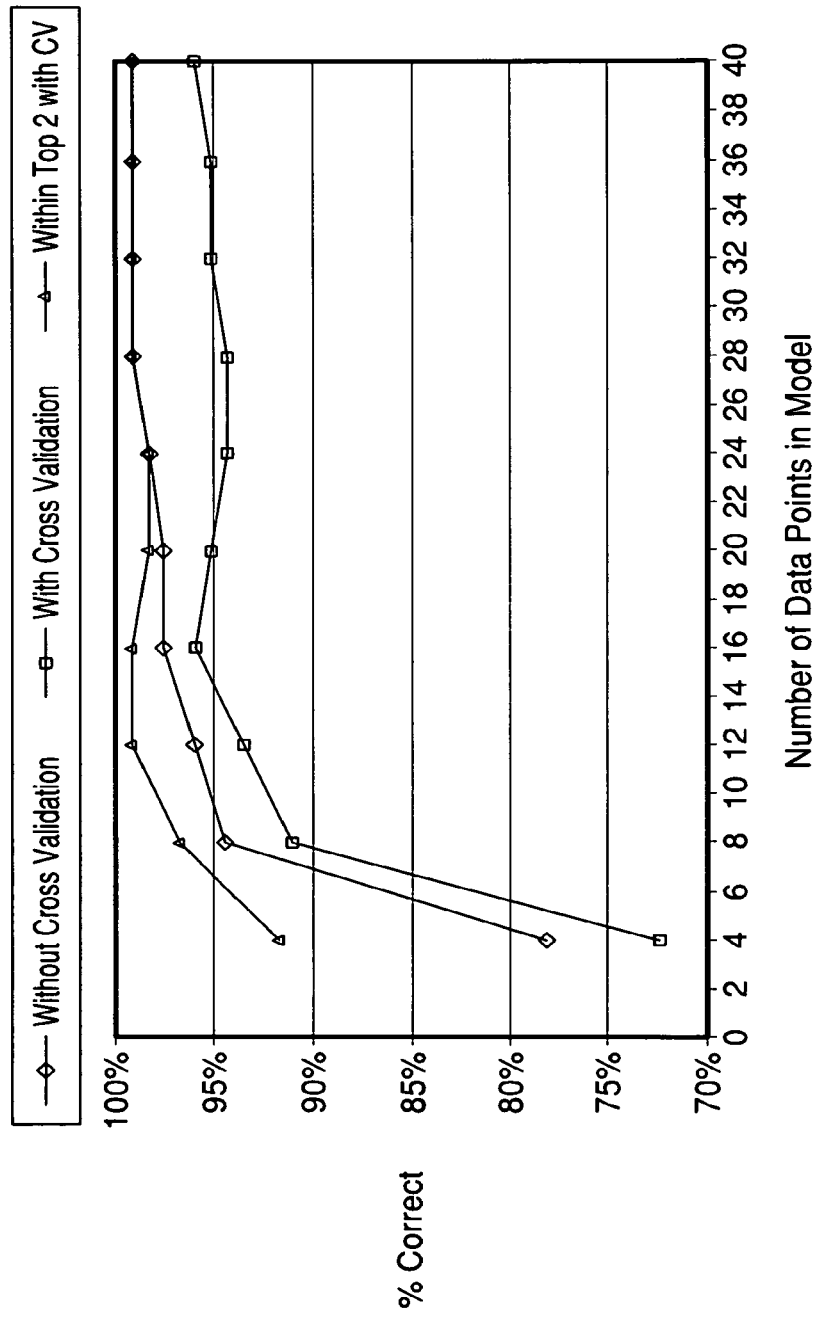

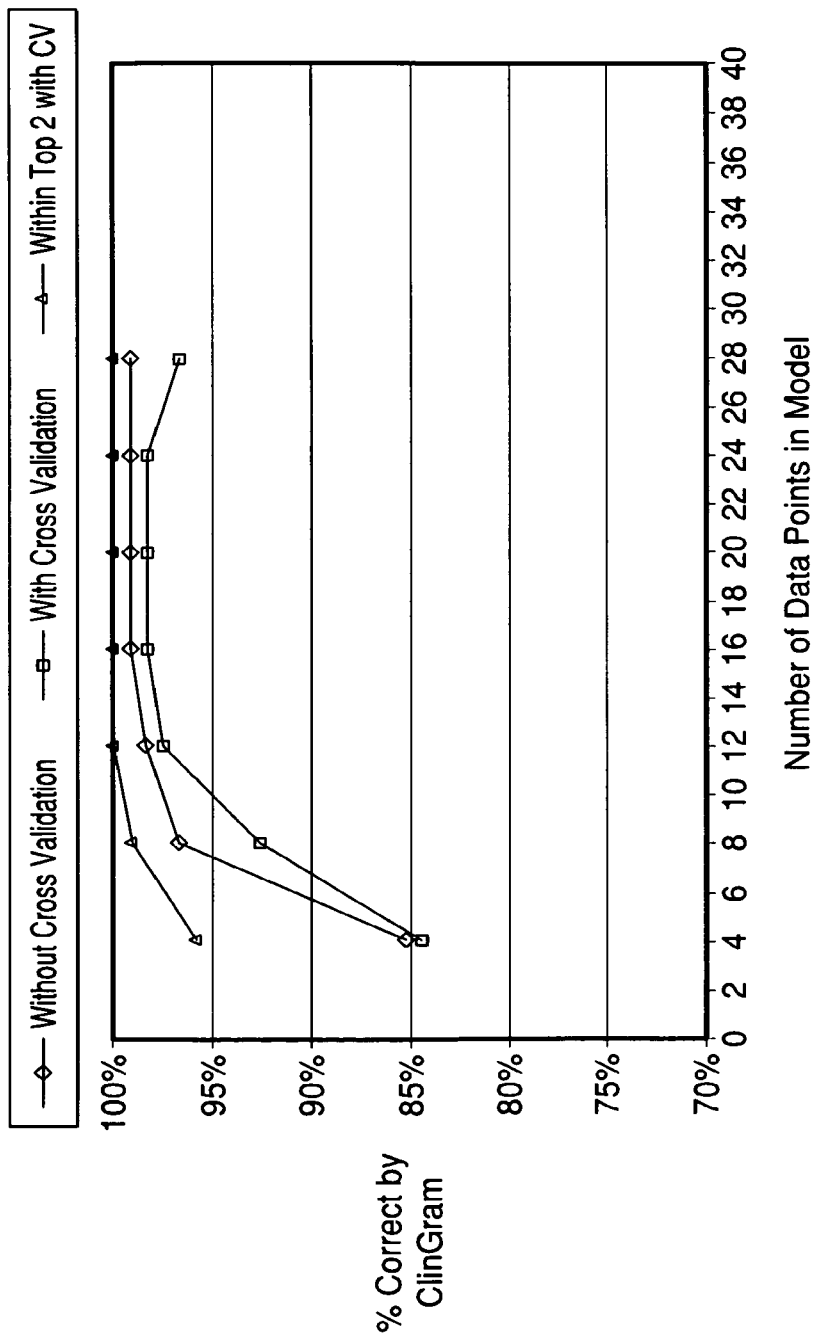

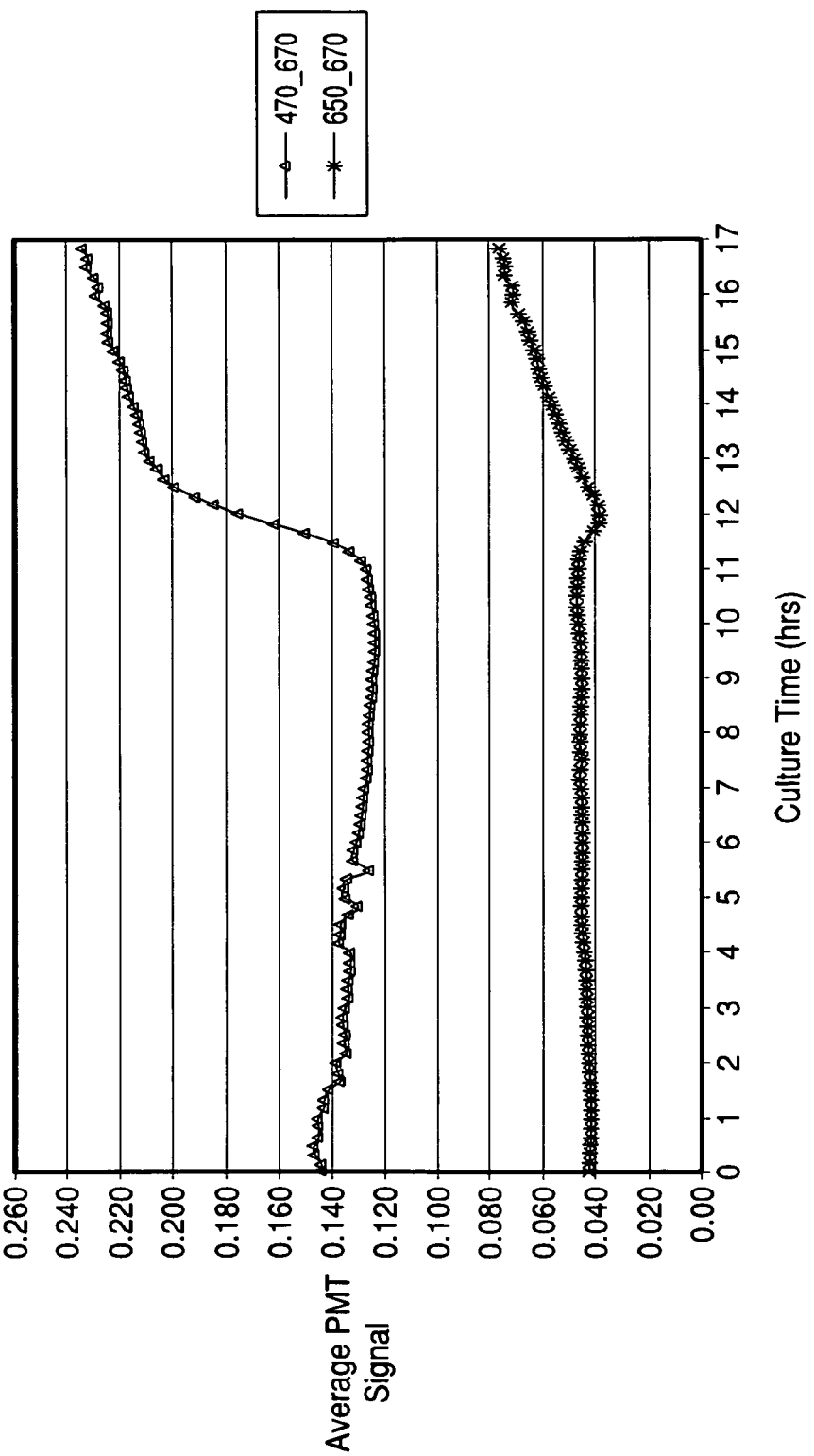

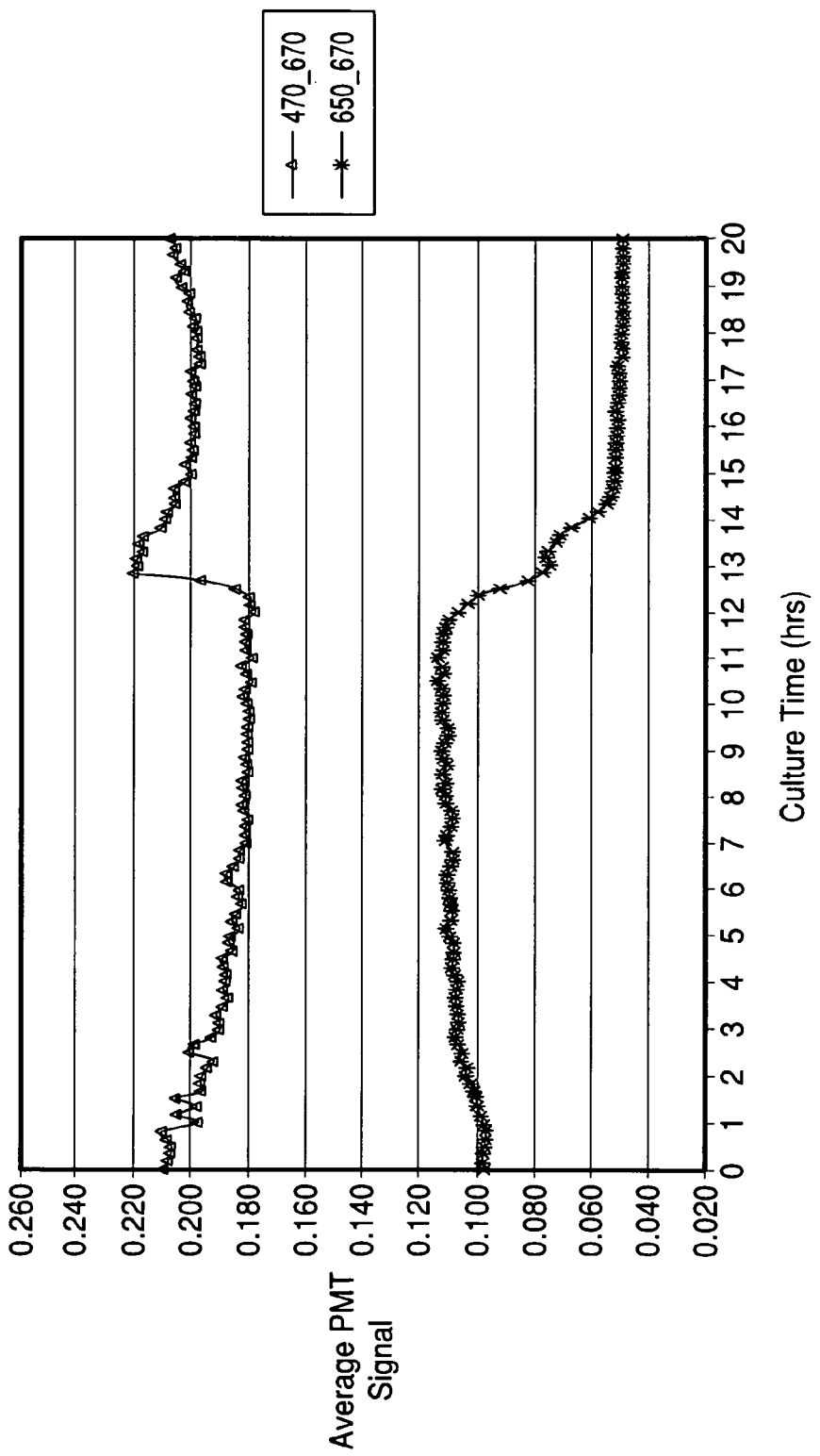

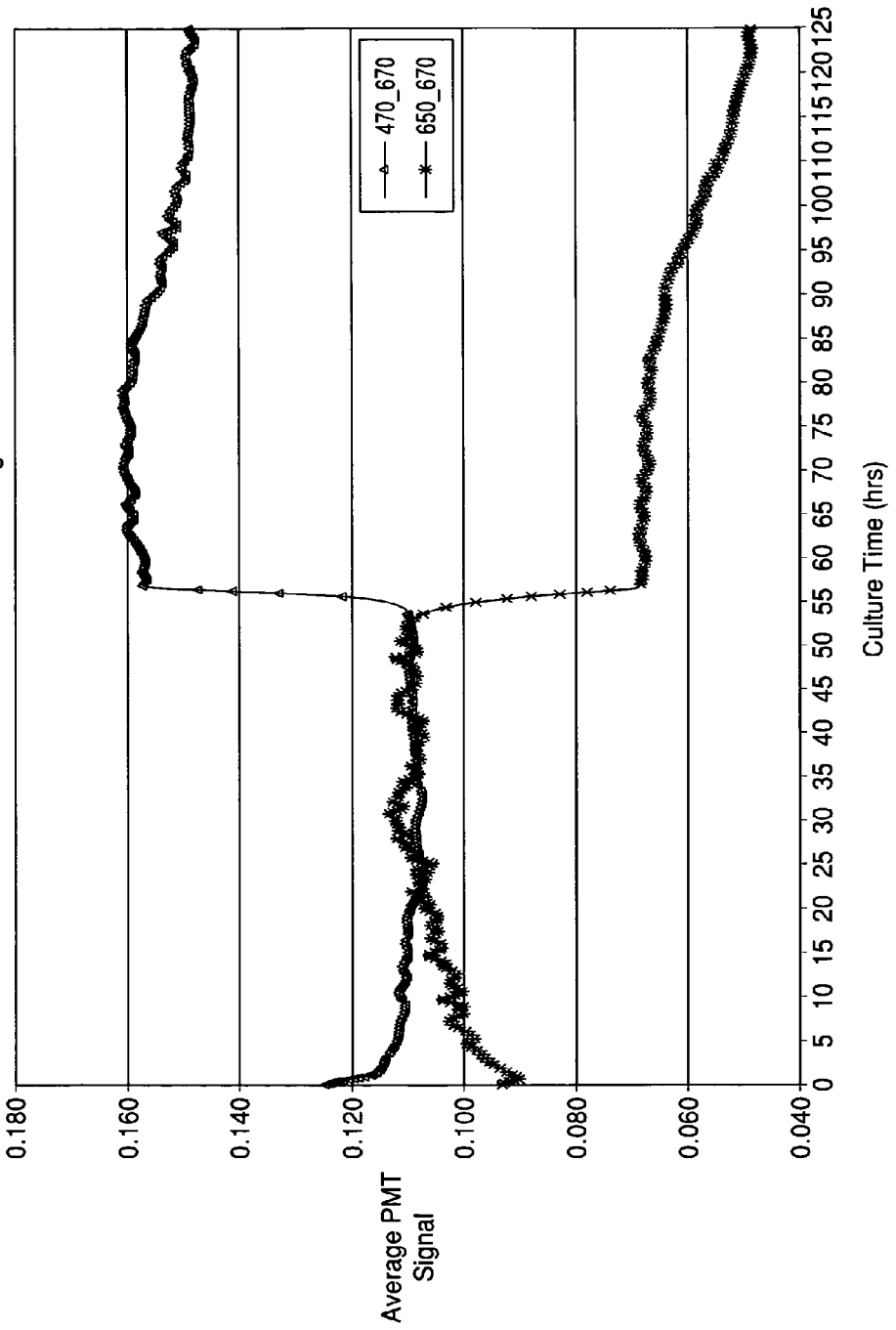

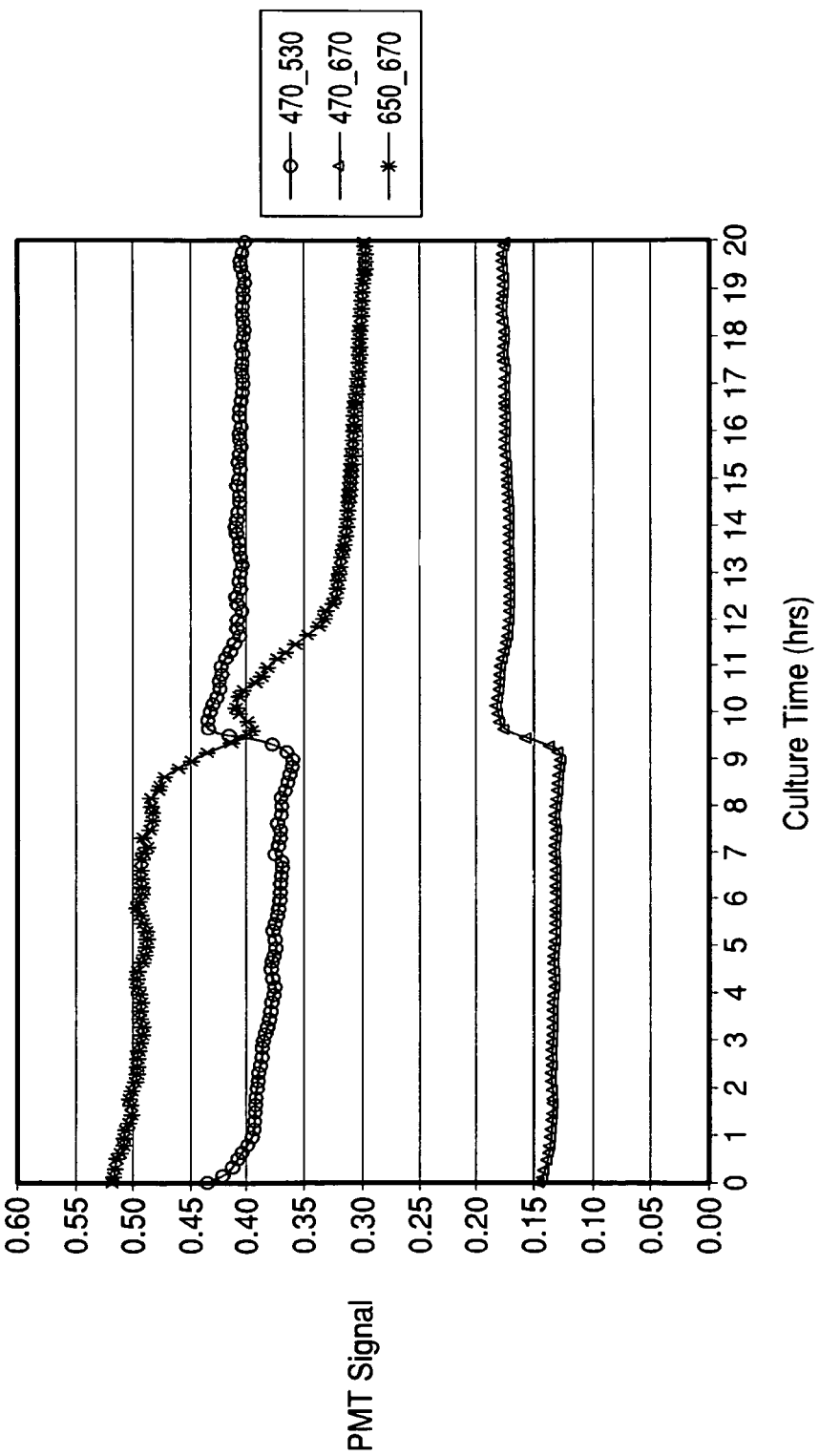

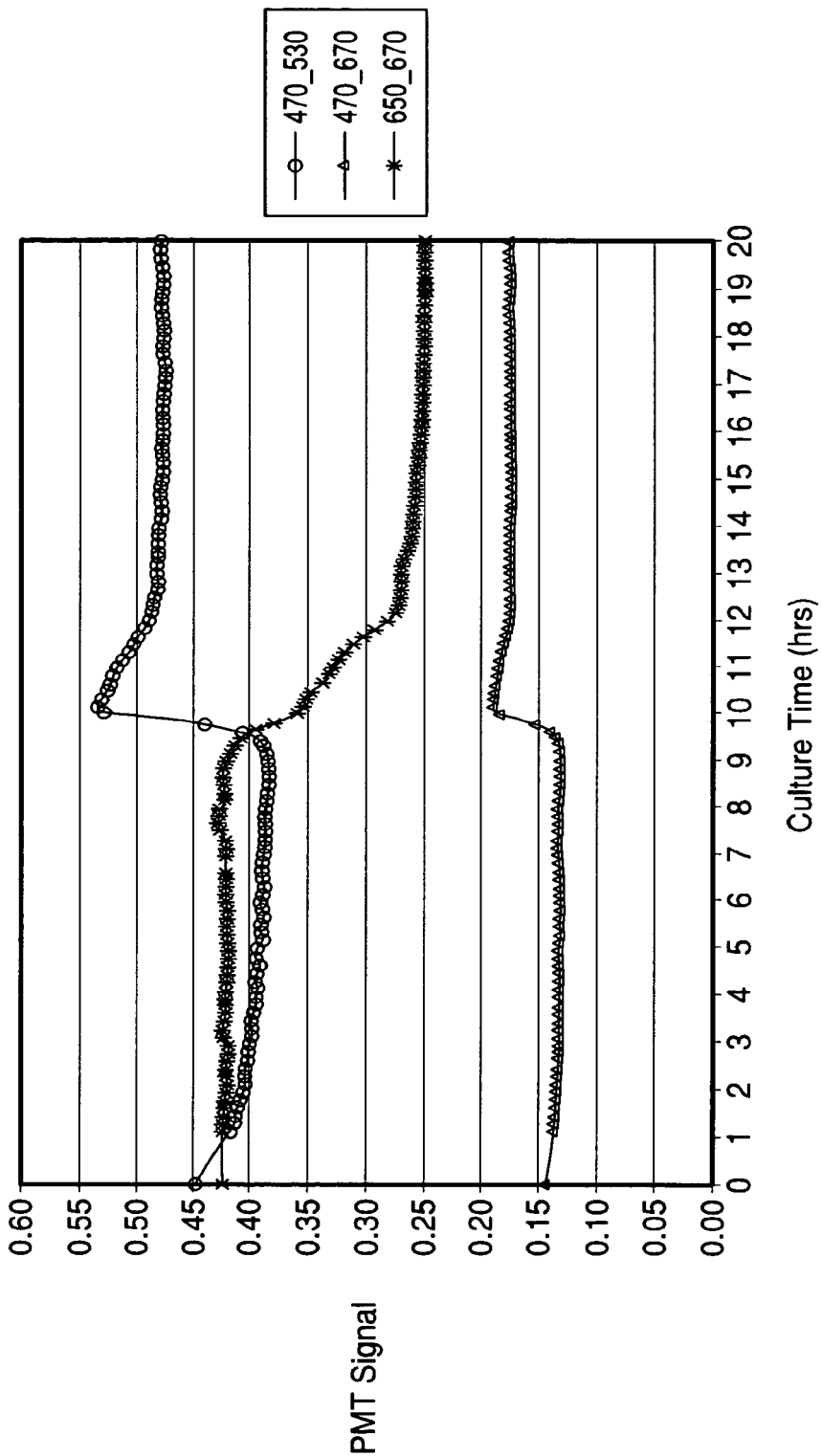

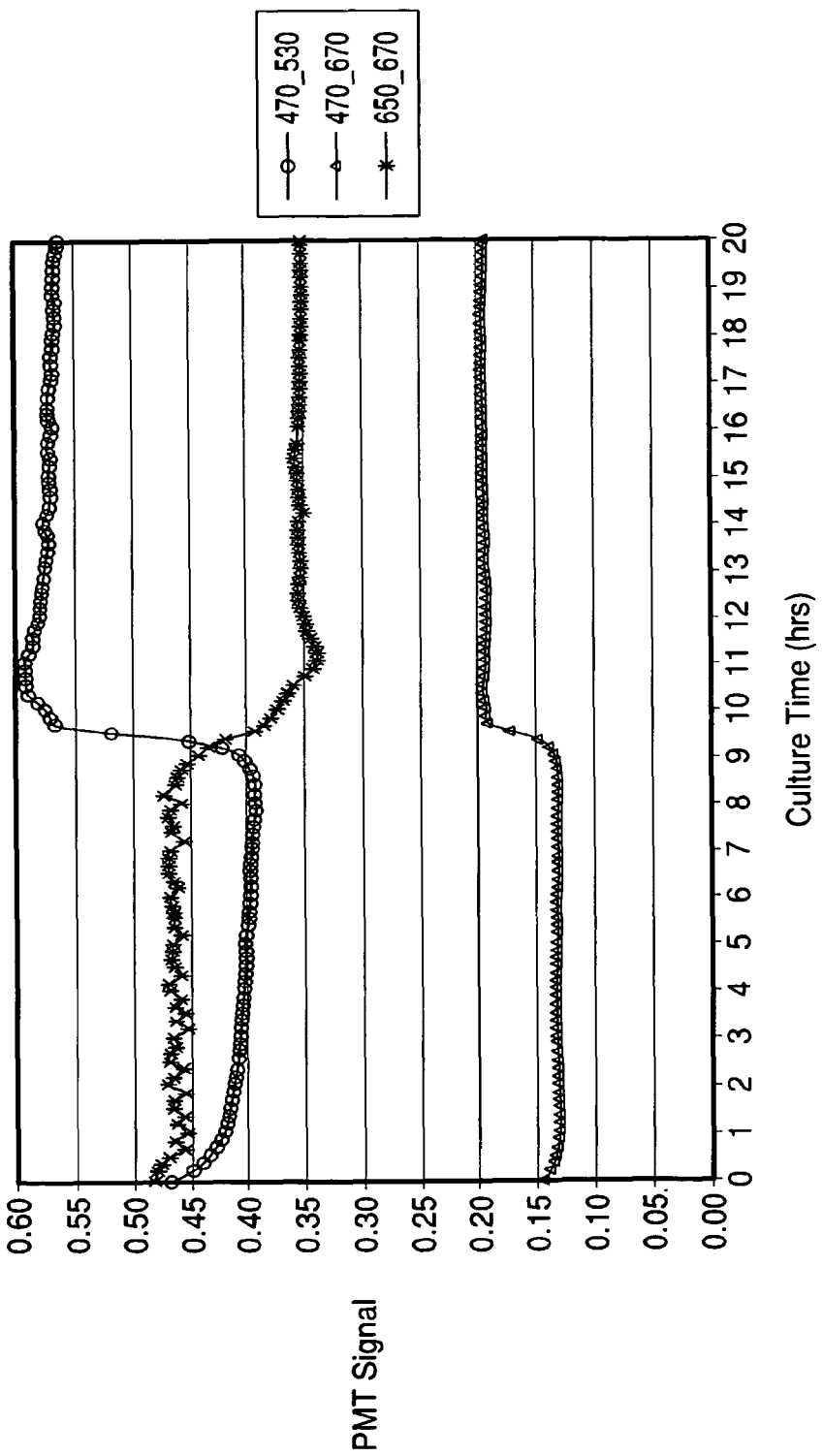

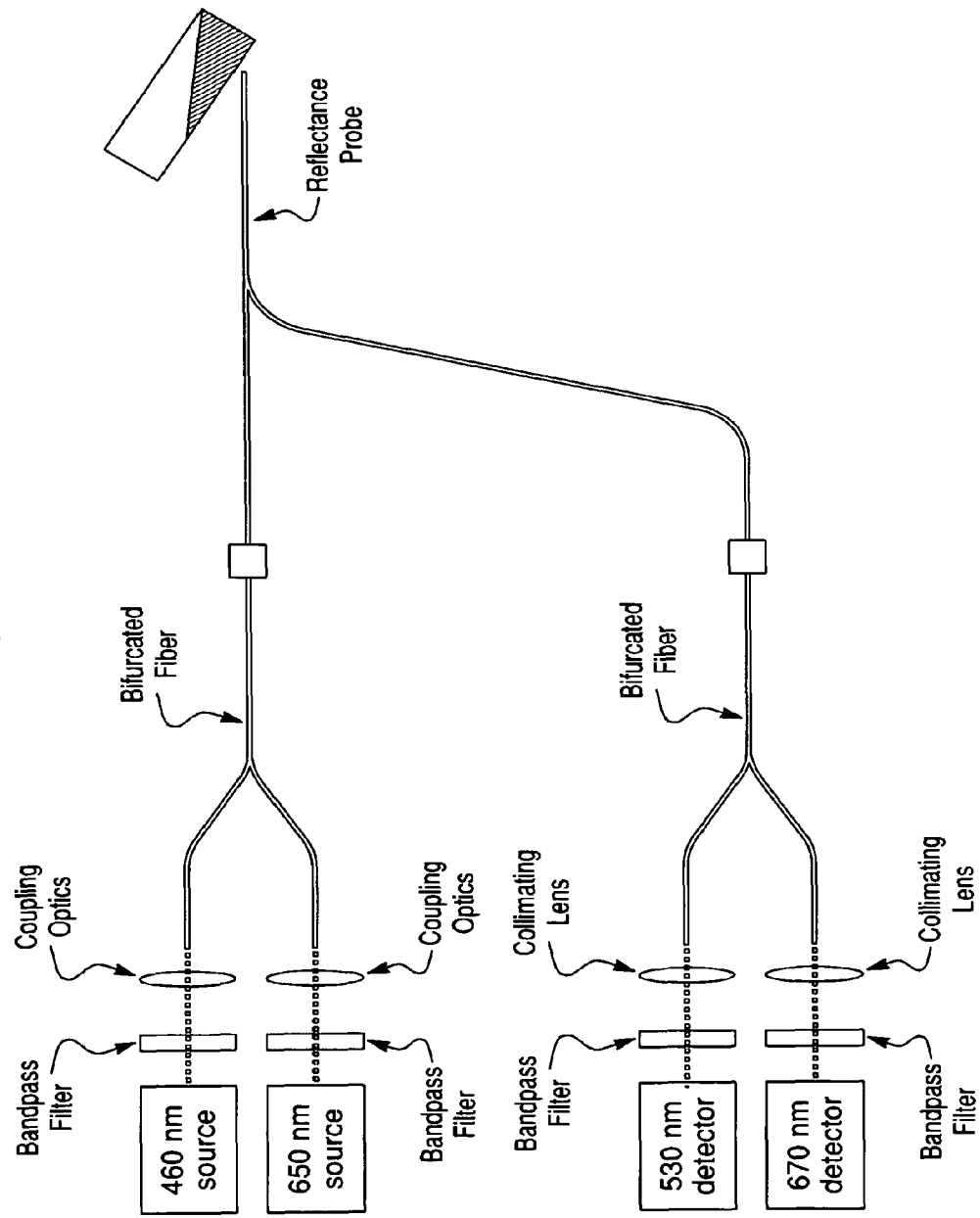

METHOD FOR DETECTION AND CHARACTERIZATION OF A MICROORGANISM IN A SAMPLE USING TIME-DEPENDENT INTRINSIC FLUORESCENCE MEASUREMENTS

CROSS REFERENCE TO RELATED APPLICATIONS

This application is being filed as a continuation of U.S. patent application Ser. No. 12/460,607, which was filed Jul. 22, 2009, is pending, and claims the benefit of U.S. Provisional Patent Application No. 61/135,839, entitled, "Method and System for Detection and/or Characterization of a Biological Particle in a Sample", filed Jul. 24, 2008.

FIELD OF THE INVENTION

The present invention relates to a method and system for monitoring, detecting and/or characterizing a sample for biological particle growth.

BACKGROUND OF THE INVENTION

Methods to detect and identify microorganisms are typically conducted on separate automated systems in clinical laboratory and industrial settings. Standard automated blood culture instruments are restricted to a detection system that gives either a positive or negative result but does not provide any information about the characterization or identity of the microorganism. Aside from testing with molecular based assays, which are expensive and generally limited to specific microorganisms, the identity of the microorganism is typically established by taking a sample from a positive blood culture bottle and conducting a separate identification test, usually after an overnight subculture step to prepare the organisms for identification testing.

WO2007/019462 generally relates to a method for the identification and quantification of a biological sample based on measurement of a fluorescence Excitation-Emission Matrix (EEM) at a single time point. The sensitivity of this approach is limited because the quenching, fluorescence, and reflectance properties of the surrounding medium within which the biological sample of interest is contained can interfere with the measurement. If the microorganism is in a homogeneous and transparent sample, such as water or saline, the system is operable. However, for turbid, optically dense, or other complex samples, such as blood, the system is inefficient because the variability of the complex background complicates the microorganism spectrum when measured at only a single time point. Small changes in reflectance and fluorescence of the microorganism cannot be measured with a single EEM reading because the variability in background signals of turbid samples is greater than the specific signal emitted by the microorganism. Thus, sensitive detection and early characterization or identification of the biological entity in a complex sample is generally not practical with a single measurement approach as taught by this reference.

There is a continued need for automated systems to provide additional capabilities in monitoring, detecting and/or characterizing biological particles, particularly microorganisms. Alternative methods for earlier detection and characterization are also desirable because there is a benefit in clinical settings to provide early results to physicians as more appropriate therapy can be selected at or around the time the blood or sterile body fluid culture is shown as positive for microbial growth. Additional information in a shortened timeframe would also be helpful for non-clinical uses of the system as well.

SUMMARY OF THE INVENTION

Provided herewith is a method and system for monitoring, detecting and/or characterizing biological particles that may be present in a sample, useful in both clinical and non-clinical settings.

In one embodiment, the method comprises utilizing a spectroscopic technique to obtain at least two time-dependent measurements of a growth composition comprising a sample and correlating said measurements to detecting and/or characterizing a biological particle if present in said sample. According to the invention, the measurements take into account changes in said growth composition as well as detecting and/or characterizing the mass of said biological particle or components thereof. The method is particularly useful for monitoring, detecting and/or characterizing microorganisms in complex sample types.

In another embodiment, the invention provides an automated system for detecting and/or characterizing a biological particle that may be present in a sample, said system comprising: (1) a growth chamber comprising a sample and a growth composition; (2) a measurement device comprising a reflectance and/or fluorescence spectrometer to enable a measurement of reflectance and/or fluorescence from said growth chamber taken at two or more time points; and (3) a means for relating said measurement to detecting and/or characterizing said biological particle if present in said sample, wherein said growth chamber is located in the same system as the measurement device and the measurement is non-invasive to the growth chamber. In this system, no manual sampling of the composition comprising a sample is required to provide early detection and/or characterization, thus providing improved efficiency and safety that may be particularly useful in both clinical and non-clinical applications.

In yet another embodiment, a method for detecting and/or characterizing a biological particle present in a sample is provided, said method comprising the steps of:
 (a) introducing a container comprising a growth composition and a sample into a diagnostic system, wherein said container may contain said growth composition and said sample either prior to introduction or after introduction of said container into said diagnostic system;
 (b) illuminating said container at predetermined time points or continuously;
 (c) monitoring said illuminated composition at predetermined time points or continuously to obtain at least two measurements, wherein said monitoring is conducted at a wavelength equal to or longer than the wavelength used in illumination, for reflectance and fluorescence, respectively; and
 (d) correlating said measurements to detect and/or characterize said biological particle if contained within said sample.

In still a further embodiment, a system for detecting and/or characterizing biological particle growth is provided, said system comprising: (1) a sealed container comprising a sample, a growth composition, and a sensor to non-invasively detect growth of said biological particle; and (2) a measurement means, such as a spectroscopy apparatus, to provide at least two time-dependent measurements of reflectance and/or fluorescence of said container in a non-invasive manner wherein said spectroscopy apparatus provides measurements of both changes in sample as well as changes in said growth composition over time; and (3) a means to correlate said measurements to the detection and/or characterization of biological particles if present in said sample. This method is particularly effective in a highly scattering and strongly fluorescent environment as found in complex sample types such as blood and other opaque substances. In this system, the combination offers diversity within a single system thus providing the test to a wider variety of sample types, as discussed in more detail hereinafter.

BRIEF DESCRIPTION OF FIGURES

FIGS. 1A and 1B illustrate time-dependent changes in fluorescence signals of seeded blood cultures containing *E. coli* and *S. aureus*, respectably, at several selected wavelengths.

FIGS. 2A and 2B illustrate time-dependent changes in scattering signals of seeded blood cultures containing *E. coli* and *S. aureus*, respectably, monitored at an excitation wavelength of 465 and emission wavelength of 465 nm (Ex465/Em465).

FIG. 3 illustrates the percent change in fluorescence signal over time in an *E. Coli* seeded blood culture with excitation wavelengths of 310-320 nm and emission wavelengths of 345-530 nm.

FIGS. 4A and 4B illustrate the Excitation-Emission Matrix (EEM) measurements data obtained from monitoring the fluorescence of an *E. coli* seeded blood culture, and demonstration of "Early" phase data (FIG. 4A) and "Late" phase data (FIG. 4B), respectively.

FIG. 7 illustrates a classification model using general discriminate analyses of microbial group-specific changes in fluorescence emission using seventeen excitation/emission wavelength pairs.

FIGS. 8A-8D illustrate examples of different microorganisms with characteristic fluorescence patterns, with FIG. 8A illustrating a Negative Control, FIG. 8B illustrating *E. faecalis* seeded blood culture, FIG. 8C illustrating *P. aeruginosa* seeded blood culture, and FIG. 8D illustrating *S. pneumoniae* seeded blood culture.

FIGS. 9A-9D illustrate examples of different microorganisms with characteristic diffuse reflectance patterns at varying wavelengths, with FIG. 9A illustrating a Negative Control, FIG. 9B illustrating *E. faecalis* seeded blood culture, FIG. 9C illustrating *P. aeruginosa* seeded blood culture, and FIG. 9D illustrating *S. pneumoniae* seeded blood culture.

FIGS. 10A-10F illustrate examples of percent change in fluorescence signal over time at selected wavelengths for different species of microorganisms.

FIGS. 11A-11D illustrate different classification models using general discriminate analyses of microbial group-specific temporal changes in fluorescence emission using different numbers of data points in the model.

FIGS. 12A-12D illustrate examples of different microorganisms with characteristic fluorescence patterns grown in commercial blood culture bottles in a proof-of-concept blood culture system.

FIGS. 13A-13D illustrate examples of different microorganisms with characteristic fluorescence patterns grown in blood culture bottles in a proof-of-concept blood culture system.

FIG. 14 is a block diagram of a proof-of-concept blood culture system.

DETAILED DESCRIPTION OF THE INVENTION

Figure 5:
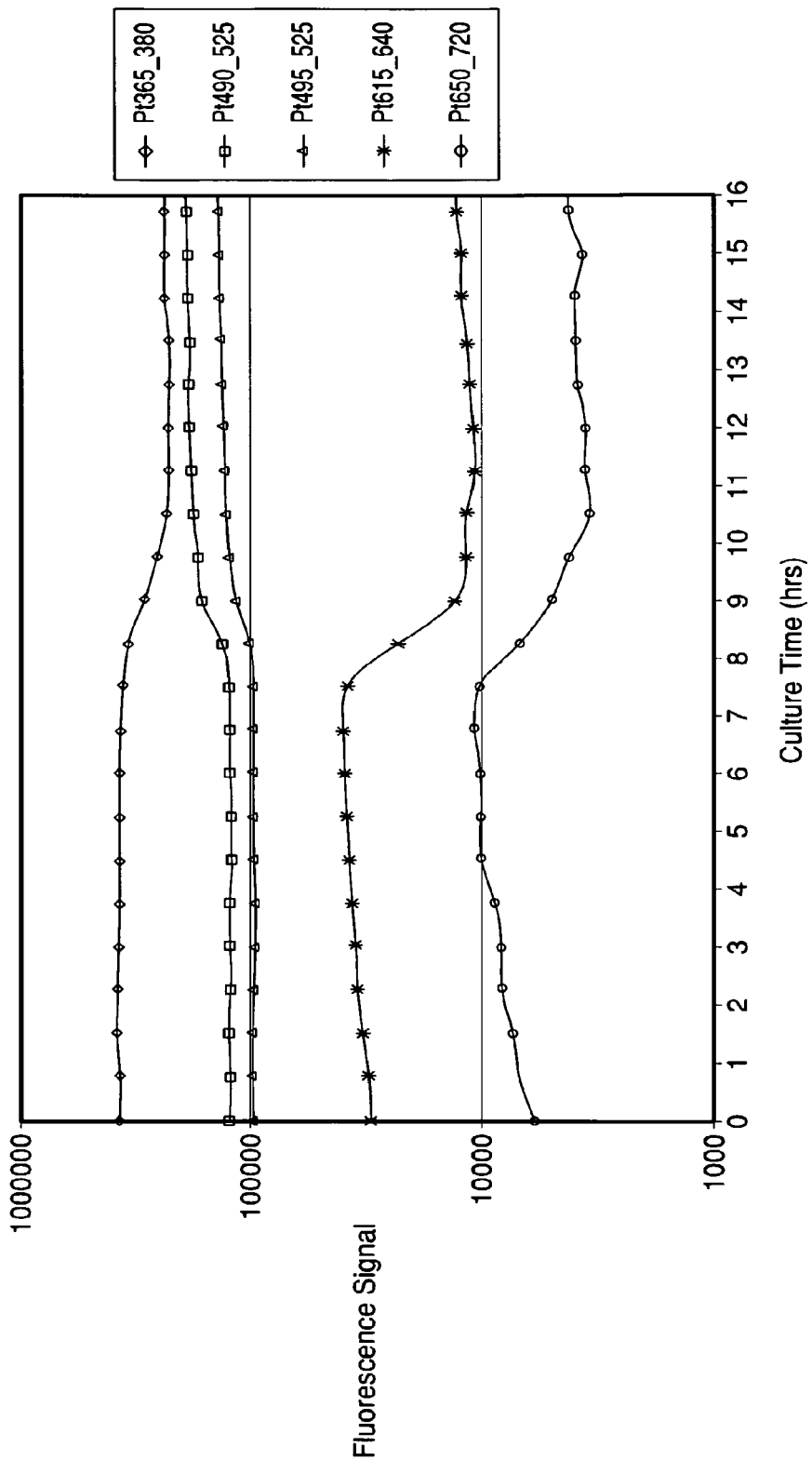
FIG. 5 illustrates time-dependent change in fluorescence of an *E. coli* culture in an ethylene oxide (EO) sterilized acrylic cuvette placed in the 22.5-degree front face waterbath adapter.

The present invention provides a means for detecting relevant levels of biological particles and components thereof in a sample. Further, characterization of the biological particles may also be accomplished based on observable differences, such as, composition, shape, size, clustering and/or metabolism. The system may be configured to monitor samples for biological particle growth, detect a biological particle in a sample, characterize a biological particle in a sample, or a combination thereof.

In a continuous analysis configuration, specific signals are determined by monitoring the fluorescence and reflectance signals of each sample, taken over time and under conditions where the concentration of a biological particle of interest generally increases from a level below the detection limit to a detectable level and may be extended to a level beyond the detection limit. Using this principle, the system measures small changes that may then be correlated with biological particle growth and may operate when the sample is of the complex and opaque type, such as a blood sample in culture media, because the method can distinguish a high background signal from the changes in both the sample and the growth composition to provide a non-invasive method for monitoring complex sample types. The kinetics of growth are captured in the method by measuring changes in the sample, changes in the growth composition, and/or the actual mass of biological particle.

Samples that may be tested include both clinical and non-clinical samples where biological particle presence or growth may be suspected. The amount of sample utilized may vary greatly due to the versatility and sensitivity of the method. Sample preparation may be accomplished by any number of techniques known to those skilled in the art although one of the advantages of the present invention is that complex sample types, defined as blood, bodily fluids, or other opaque substances, may be tested directly utilizing the system with little or no extensive pretreatment.

Clinical samples that may be tested include any type of sample typically tested in clinical laboratories, including, but not limited to, blood, sputum, plasma, blood fractions, joint fluid, urine, semen, saliva, feces, cerebrospinal fluid, gastric contents, vaginal secretions, tissue homogenates, bone marrow aspirates, bone homogenates, sputum, aspirates, swabs and swab rinsates, other body fluids, and the like.

Non-clinical samples that may be tested also include highly variable substances, encompassing, but not limited to, foodstuffs, beverages, pharmaceuticals, cosmetics, water, air, soil, plants, blood products (including platelets), donor organ or tissue samples, and the like. The method is also particularly well suited for real-time testing to monitor contamination levels, process control, quality control, and the like in industrial settings.

As used herein, the terms biological particle and biological particles are used interchangeably and intended to encompass one or more biological particle(s) and components thereof that may be detected and/or characterized in a sample, and includes any organism or cell capable of self-replication as well as fragments, metabolites, and other substances specific to organisms or cells. Encompassed in this definition are microorganisms and non-microorganisms, including, by way of example, viruses, parasites, protozoans, cryptosporidiums, and the like, including cell cultures (plant, mammalian, insect, and so on). Particularly well-suited for detection and/or characterization are microorganisms, with the term microorganism encompassing organisms that are generally unicellular, invisible to the naked eye, which can be multiplied and handled in the laboratory, including but not limited to, Gram-positive or Gram-negative bacteria, yeasts, and molds. By way of Gram-negative bacteria, mention may be made of bacteria of the following genera: *Pseudomonas, Escherichia, Salmonella, Shigella, Enterobacter, Klebsiella, Serratia, Proteus, Campylobacter, Haemophilus, Morganella, Vibrio, Yersinia, Acinetobacter, Stenotrophomonas, Brevundimonas, Ralstonia, Achromobacter, Fusobacterium, Prevotella, Branhamella, Neisseria, Burkholderia, Citrobacter, Hafnia, Edwardsiella, Aeromonas, Moraxella, Brucella, Pasteurella, Providencia*, and *Legionella*. By way of Gram-positive bacteria, mention may be made of bacteria of the following genera: *Enterococcus, Streptococcus, Staphylococcus, Bacillus, Paenibacillus, Lactobacillus, Listeria, Peptostreptococcus, Propionibacterium, Clostridium, Bacteroides, Gardnerella, Kocuria, Lactococcus, Leuconostoc, Micrococcus, Mycobacteria* and *Corynebacteria*. By way of yeasts and molds, mention may be made of yeasts of the following genera: *Candida, Cryptococcus, Nocardia, Penicillium, Alternaria, Rhodotorula, Aspergillus, Fusarium, Saccharomyces* and *Trichosporon*.

According to the invention, there is flexibility in designing the level of detection and/or characterization that the system may perform. Detection encompasses the observation of at least one change in a sample, as determined by at least two, time-dependent measurements, which may be correlated with the presence of a biological particle in the sample. Detection may occur almost immediately depending upon a number of factors including the growth rate of the biological particle, fertility of the growth composition, the selectivity of the detection algorithm, and/or the time interval of measurement, and so on. Although the actual detection times may vary depending upon these factors, preferred embodiments may provide detection of microorganisms within about 48 hours from the initiation of the method, more preferably within about 24 hours from the initiation of the method, still more preferably within the range of from about 1 hour to about 16 hours from the initiation of the method, and most preferably within the range of from about 1 hour to about 10 hours from the initiation of the method. Characterization encompasses the broad categorization or classification of biological particles as well as the actual identification of a single species. In some embodiments, classification of the biological particles of interest may require no prior knowledge of the characteristics of a given biological particle but only requires consistent correlations with empiric measurements thus making this method more general and readily adaptable than methods based on specific binding events or metabolic reactions.

More particularly, for microorganism-based applications, characterization may encompass classification of microorganisms into one or more classification models based on useful information (e.g., measurements) that may not have been otherwise available within the timeframe offered by the present method. As used herein, the preferred classification models comprise grouping or classifying microorganisms into one or more of the following: (1) Gram Groups; (2) Clinical Gram Groups; (3) Therapeutic Groups; (4) Functional Groups; and (5) Natural Intrinsic Fluorescence Groups.

(1) Gram Groups: Within the Gram Groups classification, biological particles or microorganism may be characterized into one of three broad classification categories based on their Gram staining reaction and overall size, said groups may be selected from one or more of the groups consisting of: (a) Gram positive microorganisms that stain dark blue with Gram stain; (b) Gram negative microorganisms that stain red with Gram stain; and (c) yeast cells that stain dark blue with Gram stain, but are very large rounded cells that are distinguished from the morphological characteristics of bacteria.

(2) Clinical Gram Groups: The Gram Groups may be further divided into several sub-categories representing distinguishing morphological features. These sub-categories may comprise all the relevant clinical information reported by an experienced laboratory technologist, and thus provide a higher level of identification than a positive or negative Gram reaction. This particular classification may be very helpful because it eliminates concerns about relying on the quality of a Gram stain or the skill level of the technician reading the smear by providing the equivalent clinically relevant information with an automated system. More specifically, subcategories of microorganisms based on this classification model may be selected from one or more of the groups consisting of: (a) Cocci, which are small rounded cells; (b) Diplococci, which are two small rounded cells joined together; (c) Rods, which are rectangular shape; and (d) Bacilli, which are rod shaped. Examples of additional morphological information that may be ascertained by the present invention include: (i) Gram positive cocci; (ii) Gram positive cocci in chains; (iii) Gram positive cocci in clusters (i.e., "grape-like" clusters); (iv) Gram positive diplococci; (v) Gram positive rods; (vi) Gram positive rods with endospores; (vii) Gram negative rods; (viii) Gram negative coccobacilli; (ix) Gram negative diplococci; (x) Yeast; and (xi) Filamentous fungi.

(3) Therapeutic Groups: The therapeutic groups comprise multiple microbial species that, when isolated from particular specimen types, may be treated with the same class of antibiotics or mixture of antibiotics (Reference: "*Sanford Guide to Antimicrobial Therapy* 2008"). In many cases, identity to the species level may not be required by the clinician to enable change from initial empiric therapy to a more targeted therapy because more than one species can be treated with the same choice of antibiotic. This classification level correctly places these "same-treatment" microorganisms into single therapeutic categories. Examples of this characterization level include the ability to distinguish highly resistant enterobacteriacae (EB) species from sensitive EB species (*Enterobacter* spp. from *E. coli*), or fluconazole-resistant *candida* species (*C. glabrata* and *C. kruzei*) from sensitive *candida* species (*C. albicans* and *C. parapsilosis*), and so on.

(4) Functional Groups: According to the invention, microorganisms may also be characterized into several groups based upon a mixture of metabolic, virulence and phenotypic characteristics. Non-fermentative organisms may be clearly distinguished from fermentative ones. Furthermore, microorganism species that produce typical hemolysins may be grouped separately from non-hemolytic species. In some cases, these groups may represent broader categories than genus level (e.g., coliforms, Gram negative non-fermentative rods), in some cases at the genus level (e.g., *enterococcus, candida*), and in some cases closer to species-level discrimination (e.g., coagulase-negative staphylococci, alpha-hemolytic streptococci, beta-hemolytic streptococci, coagulase-positive staphylococci, i.e., *S. aureus*).

(5) Natural Intrinsic Fluorescence ("IF") Groups: Microorganisms may also be characterized into categories based on their innate or intrinsic fluorescence characteristics. Some of these groups may be common to Therapeutic and Functional Group categories. These groupings may be comprise individual species as *E. faecalis, S. pyogenes*, or *P. aeruginosa* that have characteristic IF signatures or may contain small groups of organisms with relatively conserved IF signatures such as the *E. coli-K. oxytoca* or *E. aerogenes-C. freundii* groups.

According to the invention, the sample is combined with a growth composition which is defined as a composition that maintains the viability and/or the growth of the biological particles capable of self-replicating to be monitored in the system, particularly in a system that includes the capability for continuous monitoring. Depending upon the use of the system, the growth composition may comprise sufficient nutrients to promote rapid growth of the biological particles thereby facilitating earlier detection and characterization. For example, growth compositions may comprise media (including agar), liquid culture media (ideal for many uses), or liquid suspension, and the like. Preferably, for microorganism testing, the composition comprises media, such as tryptic soy broth, brain heart infusion broth, Columbia broth and Brucella broth, as well as other general purpose complex media known to those skilled in the art, and may include the addition of blood substitutes and specific growth factors. Additionally, ready-to-use specially formulated aerobic and anaerobic culture media for the cultivation of a variety of microorganisms may be incorporated into the system per the requirements of the organisms of interest. Standard blood culture media is preferred for more generalized testing, with the fertility of the media and selectivity of the media adjusted as within the skill of those familiar with the art. Compositions whereby the microorganisms grow in a non-homogenous or particulate manner (e.g. Mycobacteria, molds) may also be employed. Adsorbent materials, such as resins, charcoal, Fuller's earth, and the like, may be included in the composition to mitigate the effects of samples exposed to antibiotics, as is well known to those skilled in the art.

While the system is adaptable to different growth compositions and sample types, the system is preferably adapted for the variability. For example, when the sample comprises blood, algorithms or other means for modeling take into account the background such that the growth of the biological particle is observable.

In a preferred embodiment, the system includes one or more growth chamber(s) that comprise a temperature-controlled compartment that typically contains one or more containers comprising a sample and growth composition. Optionally, the growth chamber may have an agitation mechanism to provide optimal culture conditions for the growth of the biological particles, most preferably microorganisms. Appropriate growth conditions are known to those skilled in the art. Both the quantity of sample and composition in a container may be controlled depending upon design preferences and the organism of interest. For example, the system may include a control component (such as an optical sensor) to regulate the quantity of sample added to the container in an automated manner. The sample and/or composition may have already been included in the container prior to introduction into the system and samples may include those that have had growth without continuous monitoring prior to introduction into the system.

The physical features of the container of the system may take into account the design of the overall system, sample type, growth composition, and the like and include optical alignment features to facilitate optical reading. The container may be constructed from any material that does not interfere with the growth of the biological particle and does not interfere with the measurements taken. More particularly, the container may be constructed from a material that has good transmission characteristics in the UV, visible and/or infrared region of electromagnetic spectrum, with the transmission characteristics present in at least the region where the measurement occurs. For example, the material may include any UV-VIS-IR transparent material, such as glass or plastic, and ideally will have low gas permeability. The material may be single or multi-layer, where preferably at least one layer has low gas permeability. The container may be sealed or unsealed and include other desired features within such as a temperature sensor, carbon dioxide sensor, oxygen sensor, colorimetric sensors, combinations thereof, and the like. For example, the container may have a sensor, preferably an indwelling sensor, to monitor the temperature of the container that may be electronic or optical in nature and provide bottle temperature readings while requiring no physical contact to the container. The container may be an opened, vented, or closed system. The container may also be designed to facilitate sampling once adequate microbial growth occurs so that the biological particles may be isolated and purified for use in an ID, AST, molecular or other diagnostic test system at any time during monitoring. The container may also have an optical surface or coating for collection of fluorescence and scattered light. Additionally, the container may incorporate a calibration reference and/or an optical reference in different formats, as known to those skilled in the art. For example, the calibration may be accomplished with a feature optically embedded with the optical reference present in an inner layer or coating.

In one embodiment, a single system comprising at least two means of detecting biological particle growth has been found advantageous because the combination of a first and second means of detecting growth in one system provides a faster and more specific and sensitive microbial detection system with a broader applicability to test samples of varying composition. According to the invention, one means of detecting growth in the system comprises the time-dependent measurement of reflectance and/or fluorescent spectroscopy, as described previously, preferably in a front-face configuration. A second means of detecting growth in the system comprises a sealed container comprising a sample, a growth composition, and a sensor capable of detecting growth non-invasively. Preferably said sensor is a colorimetric sensor, more preferably a liquid emulsion sensor (LES), as known in the art. However, the time-dependent reflectance and/or spectroscopy method may provide the potential for earlier detection of highly metabolically active microorganisms, without the need for an internal sensor. Further, the multiple detection indicators (wavelength pairs) may improve system specificity while providing for non-invasive detection and/or characterization of any biological particles contained in the sample. The second means of a sealed container comprising a sensor may be optionally included to provide a robust, calibrated internal sensor that measures carbon dioxide and other compounds provided by biological particles. The second means also provides a method of detecting delayed entry positive samples, where the generated signal is not necessarily dependent upon the composition of the test sample but may be derived from the organism itself.

According to the invention, by monitoring the sample in a time-dependent manner (i.e., by taking at least two time-dependent measurements), the current invention may detect biological particle growth by measuring multiple changes in the surrounding highly fluorescent environment, and classify biological particles by continuing to monitor changes until characteristic patterns are recorded and analyzed. More particularly, the method is useful in the area of microorganism detection and/or characterization because microorganisms contain, or are composed of molecules that fluoresce naturally, depending on specific cell composition and metabolism. The resultant patterns differ by organism type and thus provide a fingerprint per organism type.

Preferably, the system is designed so that the user is automatically notified when a biological particle is detected in a sample. Further characterization may be made of the biological particle, as desired.

Once detection occurs, or once the sample has been identified as having biological particles present, it has been found that measurable differences can form the basis of a method for biological particle characterization early in the growth phase, sometimes almost instantaneous. Characterization patterns may emerge rapidly after the initial detection, depending upon multiple factors including sample type, sample concentration, organism concentration in sample, type of growth composition, growth rate of the organism, time interval of measurements, and so on. An automated signal may be provided in the system to notify the user upon the characterization of the biological particle, once the biological particle has been characterized into one or more characterization groups (as described herein) or identified by species, etc. In one preferred embodiment, the method automatically detects and characterizes microorganisms present within a complex, highly fluorescent and/or optically dense sample, with characterization specific to at least the level of information provided by a standard Gram stain in the case of bacteria and yeasts. Classification information may be extracted at any point during the growth of the biological particle once the sample is introduced into the system.

Preferably characterization occurs within about 48 hours of initial detection, more preferably within about 24 hours of initial detection, still more preferably within about 0 to about 16 hours of initial detection, and most preferably within from about 0 to about 8 hours post initial detection. For example, characterization may begin to occur in "early phase" (change occurring from about 0 to about 2 hours post initial detection or positive growth signal) and/or "late phase" (change occurring from about 2 to about 8 hours post initial detection or positive growth signal). Early phase tends to show patterns where spectra are dominated by changes in the growth composition. Late phase typically shows patterns where spectra are dominated by the biological particle mass rather than by changes in the growth composition.

The length of time in which monitoring the sample may occur may vary widely according to the needs of the user. For example, testing may occur for a period of time between testing initiation to days or even months, depending upon the biological particle of interest, etc., as known to those skilled in the art.

When monitoring for biological particle growth, preferably for microorganism growth, the sample may be excited as frequently as the user finds helpful for the particular testing needs, and may be automated by software. For example, for typical microorganism monitoring in blood or body fluid testing, the sample may be excited constantly or periodically. More particularly, the frequency of exciting the sample may be adjusted anywhere from constant excitation to excitation every few hours or every few days or so, more preferably within the range of exciting the sample every minute or so to every three hours, and most preferably within the range of from about every five minutes to about every hour. As used herein, excitation and illumination are used interchangeably.

Growth of the self-replicating biological particles may be monitored in real-time within a growth chamber where the readings are conducted without requiring the removal of the sample by selection of a system that is automated. While continuous monitoring is of particular usefulness, the method may be alternatively configured to monitor, detect and/or characterize biological particles present in a sample by periodic scanning, random access, and the like.

The sample illumination source, or excitation source, may be selected from any number of suitable light sources as known to those skilled in the art. More preferably, light sources capable of emission in the ultraviolet, visible and near-infrared portions of the electromagnetic spectrum are utilized and are known to those skilled in the art. For example, light sources may be continuum lamps such as a deuterium or xenon arc lamp for generation of ultraviolet light and a tungsten halogen lamp for generation of visible/near-infrared excitation. These light sources provide a broad range of emission, and the spectral bandwidth for specific excitation wavelengths may be reduced using optical interference filters, prisms or optical gratings.

Alternatively, a plurality of narrowband light sources, such as light emitting diodes or lasers, may be spatially multiplexed to provide a multi-wavelength excitation source. For example, currently, light emitting diodes are available from 240 nm to in excess of 900 nm and the sources have a spectral bandwidth of 20-40 nm (full width at half maximum). Lasers are available in discrete wavelengths from the ultraviolet to the near-infrared; many multiplexing methods are known to those skilled in the art.

The spectral selectivity of any of the light sources may be improved by using spectral discrimination means such as a scanning monochromator. Other methods of discrimination may be utilized by persons skilled in the art such as an acousto-optic tunable filter, liquid crystal tunable filter, an array of optical interference filters, prism spectrograph, etc. A consideration in selecting the spectral discriminator takes into account the range of tunability as well as the level of selectivity. By way of illustration, for example, a discriminator might utilize the wavelength range of 300-800 nm with a selectivity of 10 nm. These parameters generally determine the optimum technology necessary to achieve the tunability range as well as the selectivity.

Typically, the light source results in the excitation of the sample followed by measurement of the emission of fluorescence of the sample at predetermined time points or continuously. Similarly, the reflected light (i.e., scattered light) from the excitation source's interaction with the sample may be measured and has been shown to provide pertinent data for detection and characterization.

The emission from the sample may be measured by any suitable means of spectral discrimination, most preferably employing a spectrometer. The spectrometer may be a scanning monochromator that detects specific emission wavelengths whereby the output from the monochromator is detected by a photomultiplier tube or the spectrometer may be configured as an imaging spectrograph whereby the output is detected by an imaging detector array such as a charge-coupled device (CCD) detector array. Other methods of discrimination may be utilized by persons skilled in the art such as an acousto-optic tunable filter, liquid crystal tunable filter, an array of optical interference filters, prism spectrograph, etc. In a preferred embodiment, a discriminator allows the observation of the fluorescence and/or scattering signal by a photodetection means (such as a photomultiplier tube, avalanche photodiode, charge coupled device (CCD) detector array, or electron multiplying charge coupled device (EM-CCD) detector array).

The time-dependent spectroscopic technique is used to obtain at least two measurements that are preferably provided as Excitation-Emission Matrix (EEM) measurements. As used herein, EEM is defined as the luminescent spectral emission intensity of fluorescent substances as a function of both excitation and emission wavelength, and may include a full spectrum or a subset thereof, wherein a subset may contain a single or multiple excitation/emission pairs(s). FIGS. 4A and B show contour plots of time-dependent changes over the entire EEM spectra. Additionally, a cross section of the EEM with a fixed excitation wavelength may be used to show the emission spectra for a specific excitation wavelength, and a cross section of the EEM with a fixed emission wavelength may be used to show the excitation spectra for a sample. In one embodiment, multiple EEMs are measured at discrete points in time and using specific excitation-emission wavelength pairs.

In accordance with one embodiment, it has been found that front-face fluorescence spectroscopy provides an advantage in measuring the fluorescence and reflectance properties of highly scattering and highly quenching samples. The front-face method is particularly useful spectroscopic method because it has been found that this configuration is less affected by the interfering components of blood and microbiological culture media. In accordance with this embodiment, the optical surface of the container may be illuminated at such an angle as to provide acceptable results as known to those skilled in the art, (e.g., Eisinger, J., and J. Flores, 1983, "Front-face fluorometry of liquid samples," *Anal. Biochem.* 94:15-21). More particularly, the illumination may occur at any angle wherein the specular refection is not directed into the detector. Preferably, the system is designed such that the spectroscopy measures diffuse reflected light at a minimum of one fixed angle in addition to measuring emitted fluorescence at a minimum of one fixed angle. By way of example, the optical surface of the container may be positioned in the front-face configuration and illuminated at an angle of 0 to 90 degrees normal to the surface of the container.

According to the invention, control measurements (e.g., fluorescence and/or reflectance measurements) are taken for known biological particles (preferably microorganisms) in specific sample types thus allowing for correlation of measured test data with characterization of the biological particles of interest using various mathematical methods known to those skilled in the art. For example, the data from samples may be compared with the baseline or control measurements utilizing software systems known to one skilled in the art. More particularly, the fluorescence and scattering data may be analyzed by a number of multivariate analysis methods, such as, for example, General Discriminant Analysis (GDA), Partial Least Squares Discriminant Analysis (PLSDA), Partial Least Squares regression, Principal Component Analysis (PCA), Parallel Factor Analysis (PARAFAC), Neural Network Analysis (NNA) and Support Vector Machine (SVM). These methods may be used to classify unknown biological particles of interest (preferably a select group of microorganisms) into relevant groups based on existing nomenclature, or into naturally occurring groups based on the organism's metabolism, pathogenicity and virulence in designing the system for monitoring, detecting and/or characterizing the organism as described previously.

In a preferred embodiment, the system detects microorganisms using change in intrinsic fluorescence and/or reflectance of the culture media and sample, taking into account the growth of the microorganism itself and the changes in the kinetics due to metabolism of the microorganism in the culture. The intrinsic fluorescence or auto fluorescence of the microorganism, particularly bacteria, leverages the fact that the bacteria contain natural fluorophores such as aromatic amino acids (e.g., tryptophan, tyrosine, phenylalanine) that can be excited via a multi-wavelength light source.

The container used in the system to hold the sample may further comprise a combined $CO_2$ or other sensor that may be included for any number of reasons, including, but not limited to, compatibility with previous systems; contamination detection during manufacturing, transport or storage; and accommodation of delayed entry of bottles into an incubation/reading system. Still further, the container may have included a radio frequency identification device, barcode, or the like to store data from an initial read of the bottle at time of sample collection (including time), information from a test (could be used for post characterization), manufacturing information (lot, date, expiration, initial readings, etc.), patient and sample information at time acquired at the time of collecting the sample, and the like.

The present invention is further detailed in the following examples, which are offered by way of illustration and are not intended to limit the invention in any manner. Standard techniques well known in the art or the techniques specifically described below are utilized.

EXAMPLES

A Fluorolog 3 fluorescence spectrophotometer system (Horiba Jobin-Yvon) was modified with a temperature-controlled front-face cuvette holder to enable the incubation and continuous monitoring of seeded blood cultures contained in sterile cuvettes. The fluorescence was recorded using a photomultiplier tube. Fluorescence signal strength was taken at several different wavelengths and saved. The readings were compared to experimentally determined strengths for different types of microorganism. In addition, further analysis of the spectra was conducted so that microbial identification to a given level of confidence was achieved.

Example 1 describes seeded blood cultures in autoclaved quartz cuvettes. Ethylene-oxide sterilized acrylic cuvettes were used in Example 2. A custom-built carousel adapter that incubated the cultures at 35-37° C. and enabled multiple cultures to be performed simultaneously was used in Example 3. These experiments demonstrated that the invention possesses the potential ability to detect microorganisms in blood culture earlier than the current state-of-the art $CO_2$ sensors and has capabilities to identify the isolate at least to a clinically useful classification level. A database of EEM and scattering data from blood cultures of approximately 80 microorganism strains was built. Several multivariate analysis methods were used to classify unknown strains. The results of the General Discriminant Analysis (GDA) method are presented in Example 4. Optimization of the front-face angle for collection of blood culture EEM and scattering spectra is described in Example 5. Non-invasive invasive identification of microorganisms growing in seeded blood cultures is described in Example 6. Example 7 describes the results obtained with a Proof-of-Principle (POP) blood culture system using existing commercial blood culture bottles and continuous monitoring with multiple fluorescence and reflectance wavelengths.

Example 1

Blood Culture (Culture Medium and Blood Sample) in Quartz Cuvette in Waterbath Adapter Seeded blood cultures were set up in autoclaved 1.0 cm screw-capped quartz cuvettes (Starna, Inc.) containing a stir bar for agitation. To the cuvette was added 2.4 mL of standard blood culture medium, 0.6 mL of fresh normal human blood and 0.05 mL of a $10^3$/mL suspension of test microorganism (approx. 10 CFU/cuvette). A sterile, septum screw cap was placed on the cuvette, and it was inserted into the front-face adapter previously described. The culture was maintained at approximately 36° C. by connecting the adapter to a recirculating water bath heated to 36° C. The cuvette was read every 45 minutes by the Fluorolog 3 fluorescence spectrophotometer that was software controlled. A full EEM spectra was collected at each time point with an Excitation wavelength range of 260-580 nm (every 5 nm) and an Emission wavelength range of 260-680 nm (every 5 nm) for a total of 3,139 data-points per scan. Each scan took approximately 23 minutes to complete. The cultures were maintained, and measurements taken continuously, for up to 24 hours.

Examples of the changes in fluorescence signal of several Excitation-Emission wavelength pairs for *E. coli* and *S. aureus* cultures are shown in FIGS. 1A and 1B. It is clear that following the initial point of detection, the temporal changes occurring at these wavelengths are significantly different between the two organisms. Examples of the changes in diffuse reflectance signal at 465-465 nm for *E. coli* and *S. aureus* cultures are shown in FIGS. 2A and 2B. A clear difference in the shape of the curves over time was observed.

Further detailed examination of the changes in fluorescence from all 3,139 data-points of an *E. coli* culture revealed the presence of at least two visually-identifiable phases; change from 7-10 hrs (approximately 0-2 hours after initial detection) of culture primarily comprising the rapid initial change in the fluorescence of the culture medium, and a change from 10-15 hr (approximately 2-7 hours after initial detection) that reflects an increase of microbial intrinsic fluorophores. This phenomenon is shown in FIG. 3 as a line plot of Excitation wavelengths from about 310-320 nm and Emission wavelengths from about 345-530 nm, and in FIGS. 4A and 4B as contour plots of time-dependent changes over the entire EEM spectra. FIGS. 3, 4A and 4B demonstrate "early" and "late" phase changes that can be used for the detection and/or characterization of a biological particle. This data exemplifies the power of temporal fluorescence and scattering measurements of a growing microbial culture.

Example 2

Blood Culture in Acrylic Cuvette in Waterbath Adapter

An *E. coli* blood culture was set up as described in Example 1 with the exception that the cuvette was constructed of a UV-transparent acrylic (Sarstedt 67.755), and sterilized by ethylene oxide treatment. The change in the autofluorescence or intrinsic fluorescence of the blood-media mixture over time with multiple wavelength pairs is shown in FIG. 5.

Example 3

Blood Culture in Acrylic Cuvette in Multi-Station Carousel Adapter

Figure 6:
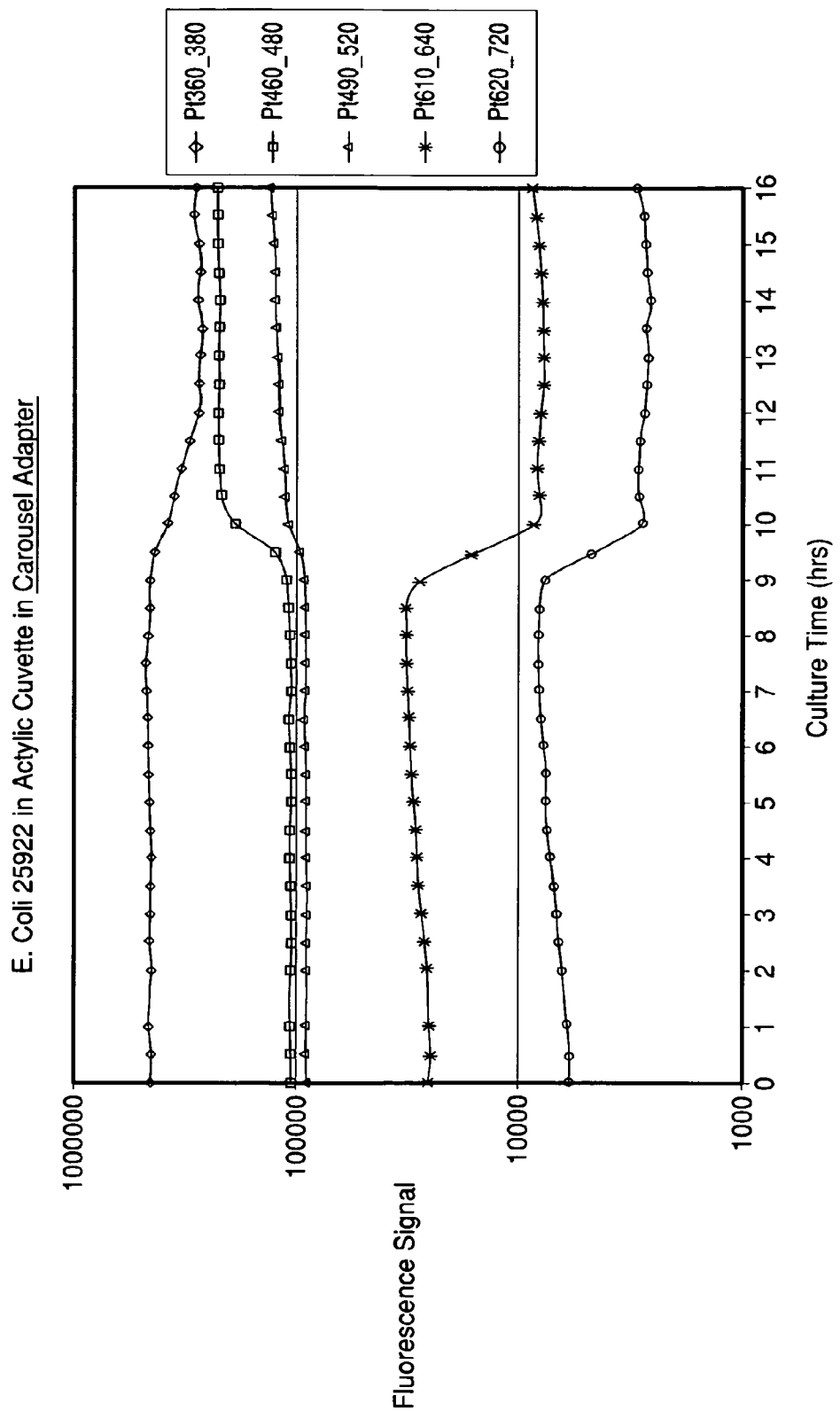
FIG. 6 illustrates time-dependent change in fluorescence of an *E. coli* culture in an EO-sterilized acrylic cuvette placed in the custom-built automated carousel adapter.

An *E. coli* blood culture was set up as described in Example 2 with the exception that the cuvette was loaded into a custom-built, temperature-controlled carousel adapter for the Fluorolog 3 system. The change in the autofluorescence or intrinsic fluorescence of the blood-media mixture over time with multiple wavelength pairs is shown in FIG. 6.

The experiments described in Examples 2 and 3 demonstrate that time-dependent changes in fluorescence were measured in readily available plastic containers and in a manner amenable to larger scale automation, respectively. The same is true for the diffuse reflectance measurements collected in these experiments (data not shown).

Example 4

GDA Analysis of Simulated Blood Culture Study (Group Level)

In this study, a sample of positive culture medium was removed from seeded BacT/ALERT® SA (bioMérieux, Inc.) blood cultures bottles within a few minutes of the BacT/ALERT® Microbial Detection System (bioMérieux, Inc.) calling the culture positive. Culture media removed from sterile blood culture bottles at similar times served as negative controls. The culture media samples were placed in acrylic cuvettes and read in the Fluorolog 3 with a full EEM scan. Fluorescence and scattering data were normalized to age-matched negative controls, and then analyzed by General Discriminant Analysis (GDA).

Measurements taken for multiple data points from each sample tested were compared to a database of EEM and reflectance data from blood cultures of 77 known microorganism strains, representing 12 species, and the tested strains were classified based on the comparisons. The percentage of strains correctly identified to the "Group" classification level based on the number of data points collected is presented in FIG. 7. FIG. 7 demonstrates that analysis of microbial-specific changes in fluorescence and scattering classified >97% of the test microorganisms correctly into clinically relevant groups based on either existing nomenclature or the organism's innate metabolism, pathogenicity and virulence characteristics.

Example 5

Optimization of the Front-Face Angle

Blood cultures of *E. coli* in acrylic cuvettes were set up as described in Example 3. The front face angle of sequential cultures was adjusted to test the following angles: 20, 22.5, 26, 30, 34 and 38 degrees. Pure suspensions of *E. coli* and *S. aureus* were also measured at each angle. The optimal front face angle was shown to be 26 degrees, when assessed as either the greatest degree of change in the *E. coli* cultures (Table 1), or as the highest absolute signals and signal to noise ratios of cellular fluorophores of the two microbial suspensions (data not shown). The values given in Table 1 represent the average signal for all Rayleigh points (260-750 nm) and all fluorescence points within the EEM. While the average Rayleigh signal in positive regions of the microbial growth curve was reduced by 66%, large increases were observed at specific wavelengths such as 465-465 nm, as exemplified in FIGS. 2A and 2B.

TABLE 1

% Change in Signal from Negative to Positive Regions of an *E. coli* Growth Curve

| | Front-Face Angle | | | | | |
|---|---|---|---|---|---|---|
| | 20° | 22.5° | 26° | 30° | 34° | 38° |
| Scattering Average | −50% | −59% | −66% | −49% | −43% | −62% |
| EEM Average | 1% | 1% | 10% | 2% | 0% | −2% |

Example 6

Non-Invasive Identification of Microorganisms Growing in Blood Cultures

A total of 119 seeded blood cultures, representing 5-15 strains of fourteen clinically-relevant species (see Table 2 below), were inoculated into sterile acrylic cuvettes and loaded into the multi-station carousel adapter for the FluoroLog 3 system.

TABLE 2

Clinically Relevant Species Tested

| | | | |
|---|---|---|---|
| C. albicans | E. coli | A. baumanii | E. faecalis |
| C. parapsilosis | E. aerogenes | P. aeruginosa | S. pneumoniae |
| C. tropicalis | K. pneumoniae | S. aureus | S. mitis |
| | P. mirabilis | S. epidermidis | |

Each culture was scanned continuously (every 30 to 35 minutes) for up to 5 days using a selection of 82 fluorescent wavelength pairs and 50 diffuse scattering wavelengths.

FIGS. 8B-8D show characteristic fluorescence patterns over a period of 23 hours for different microorganisms. The data from 4 of the 82 wavelength pairs are shown (Ex360/Em380 nm, Ex460/Em480 nm, Ex650/Em670 nm and Ex700/Em730 nm). FIG. 8A shows data collected for a Negative Control, FIG. 8B shows data collected for a E. faecalis seeded blood culture, FIG. 8C shows data collected for a P. aeruginosa seeded blood culture, and FIG. 8D shows data collected for a S. pneumoniae seeded blood culture. Obvious differences in the shapes of the fluorescent curves are evident between these three species.

Figure 9D:
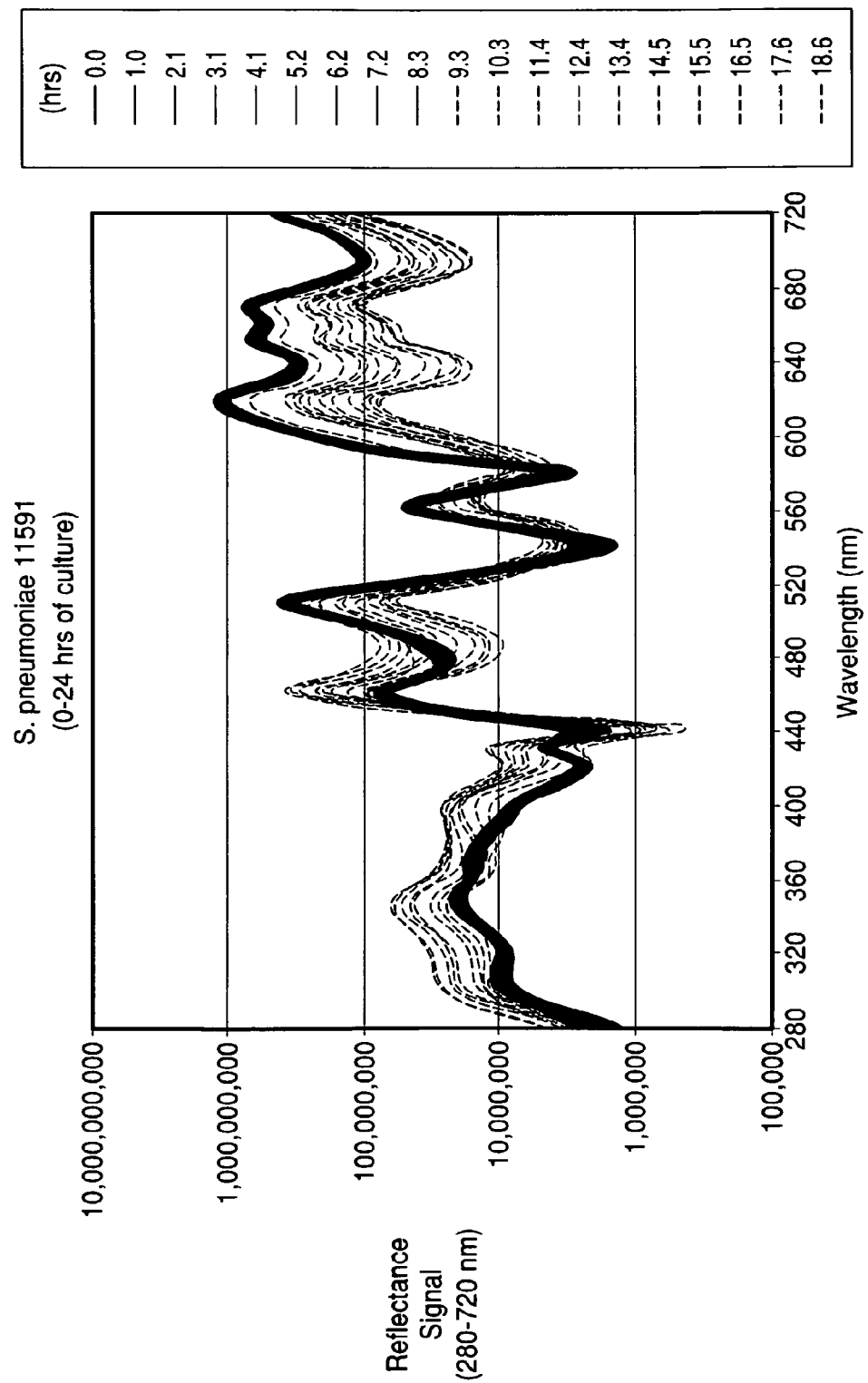

FIGS. 9B-9D show characteristic diffuse reflectance patterns at wavelengths from 280-720 nm over a 23-hour culture period for the same three microorganisms shown in FIG. 8. FIG. 9A shows data collected for a Negative Control, FIG. 9B shows data collected for E. faecalis, FIG. 9C shows data collected for P. aeruginosa, and FIG. 9D shows data collected for S. pneumoniae. Once again, distinctive patterns of reflectance emerged, as indicated by a shift away from the normal reflectance signal of the negative control (FIG. 9A). The extent and rate of this temporal shift in reflectance was characteristic for certain microorganisms.

Figure 10A:
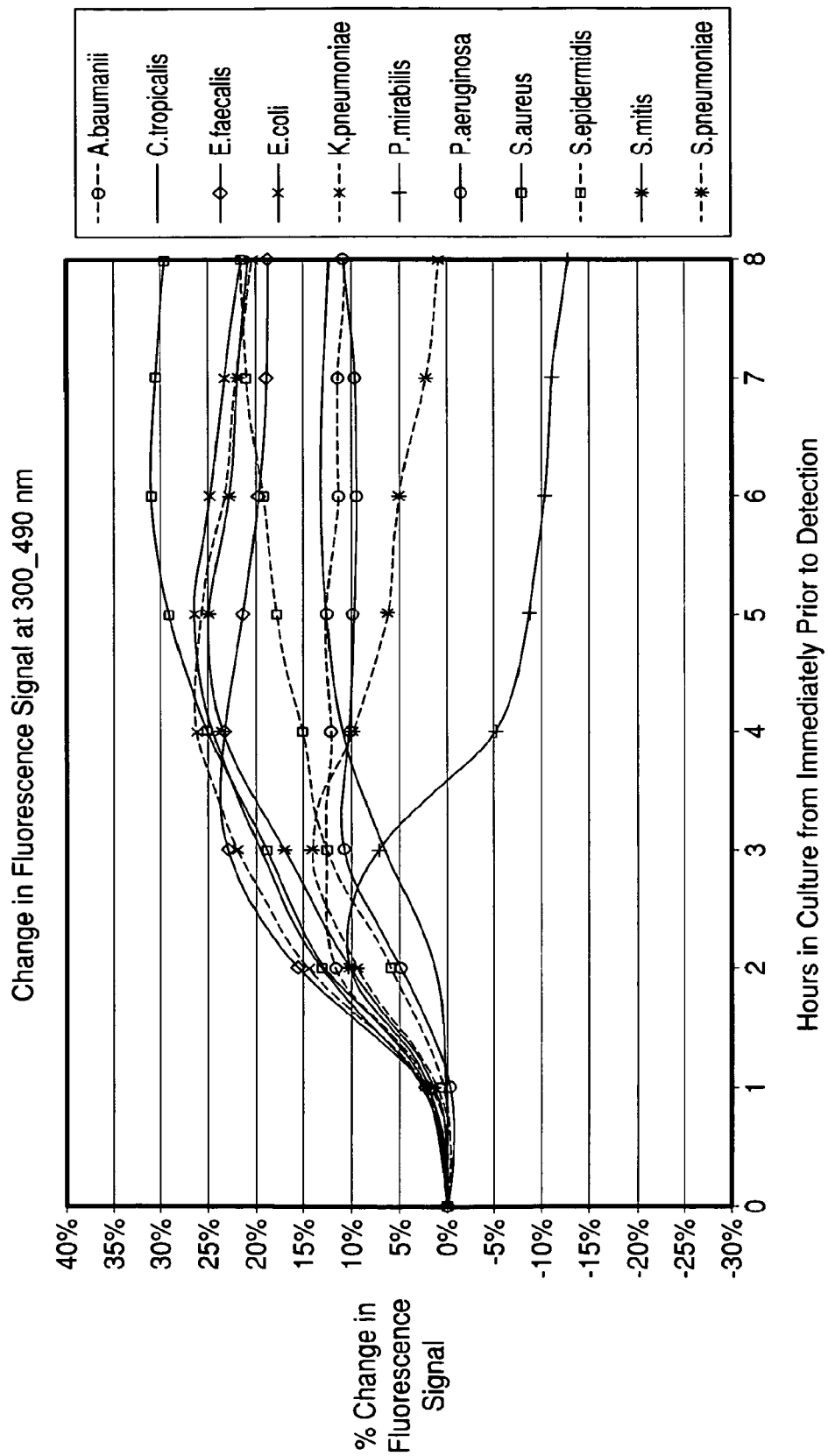
Figure 10C:
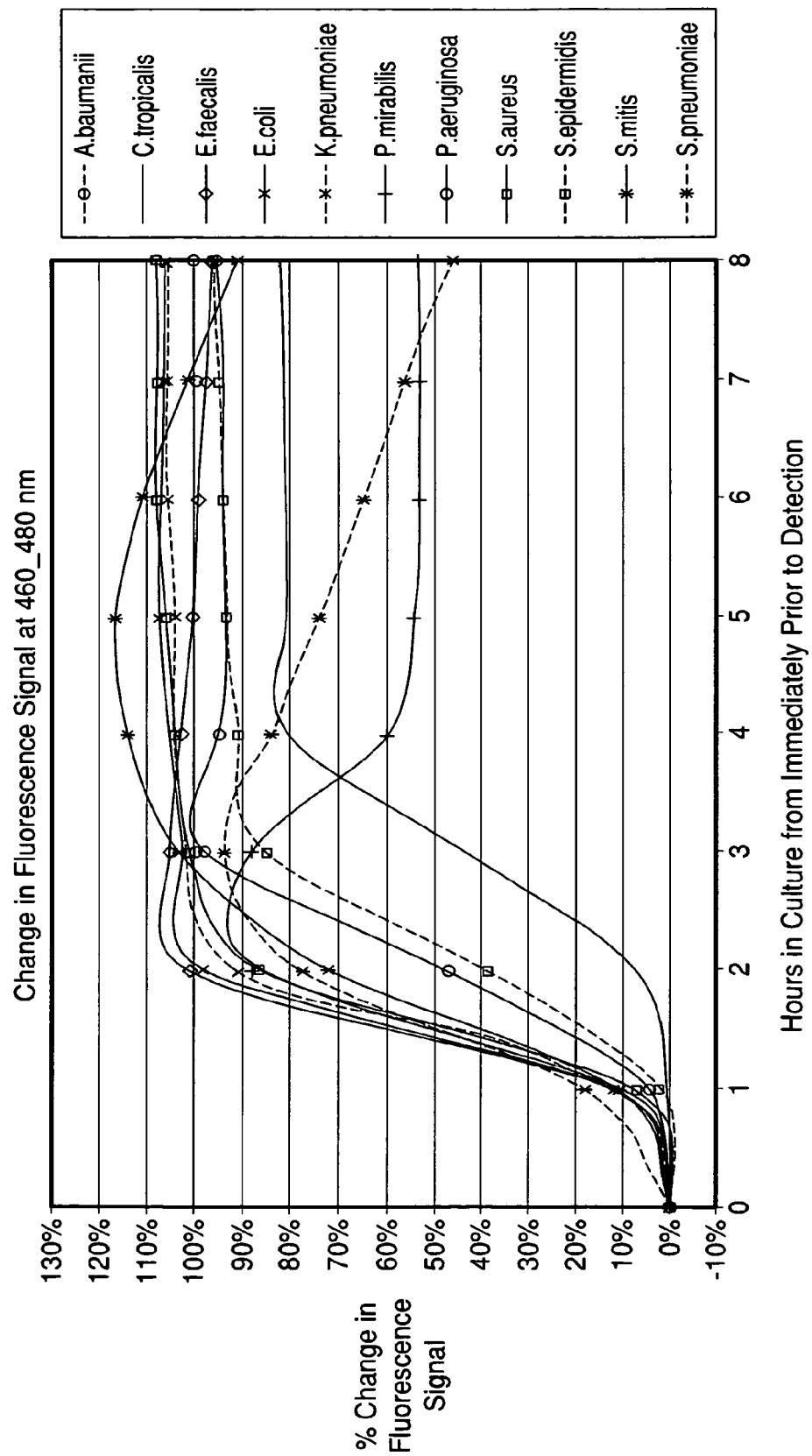
Figure 10D:
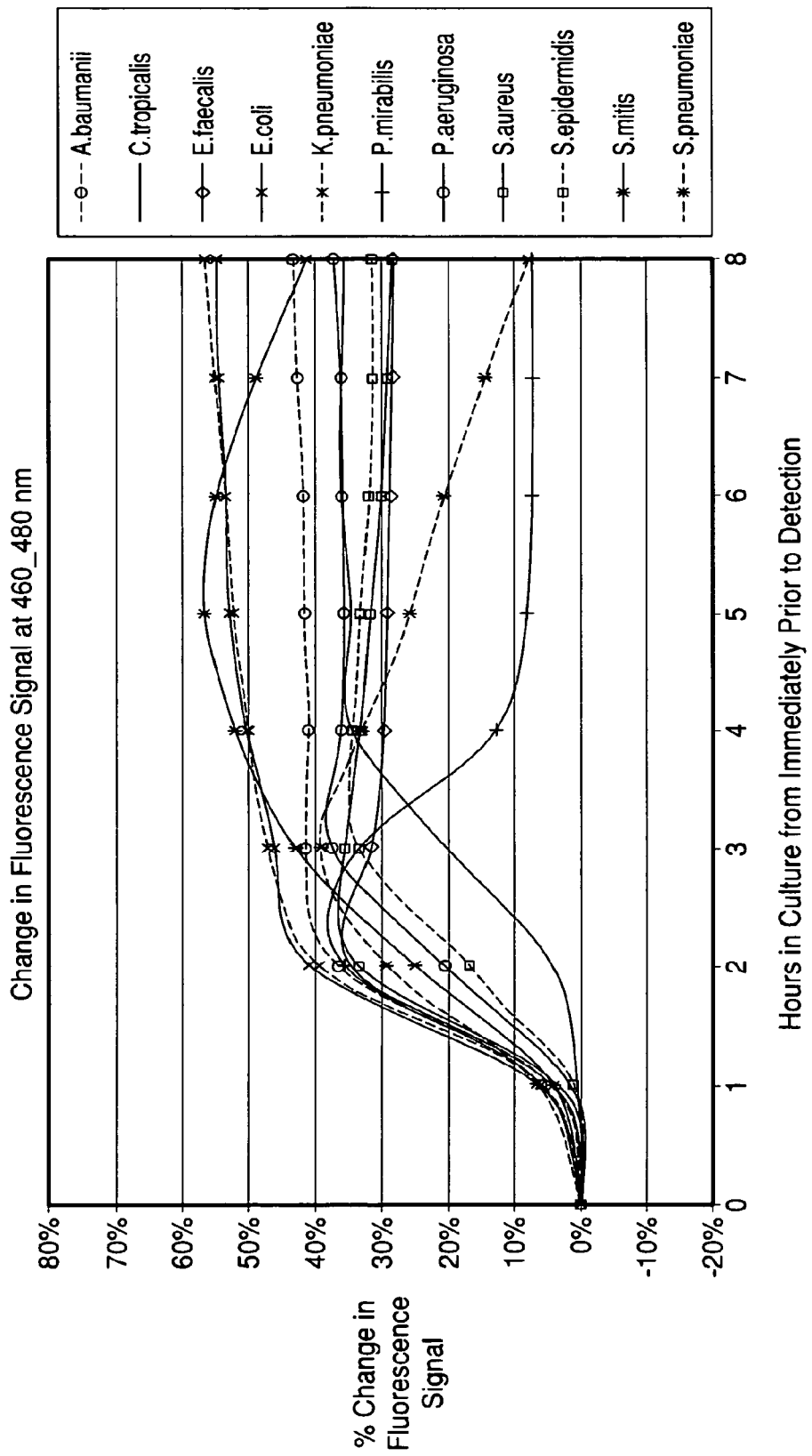
Figure 12B:
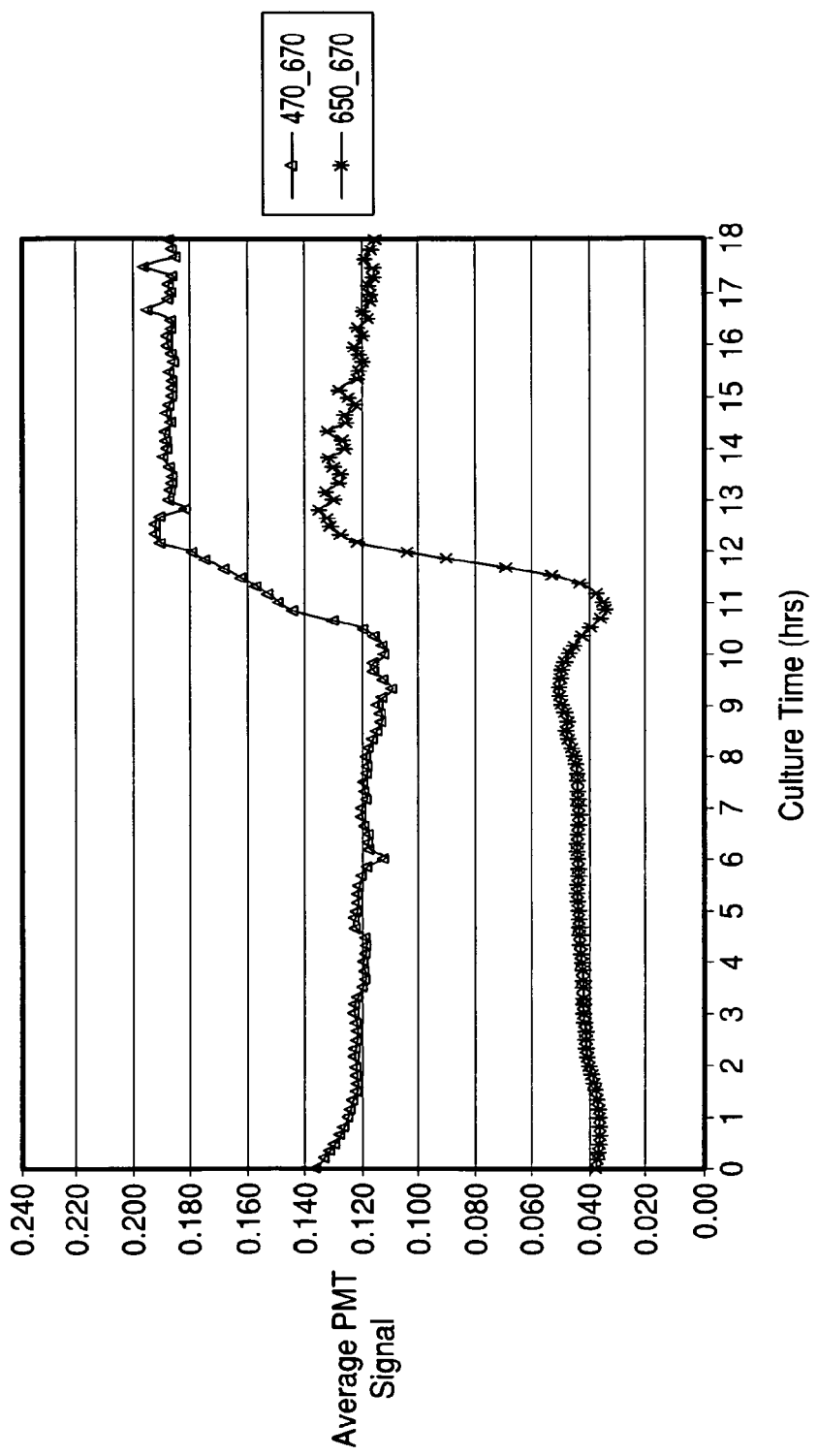
Figure 13A:
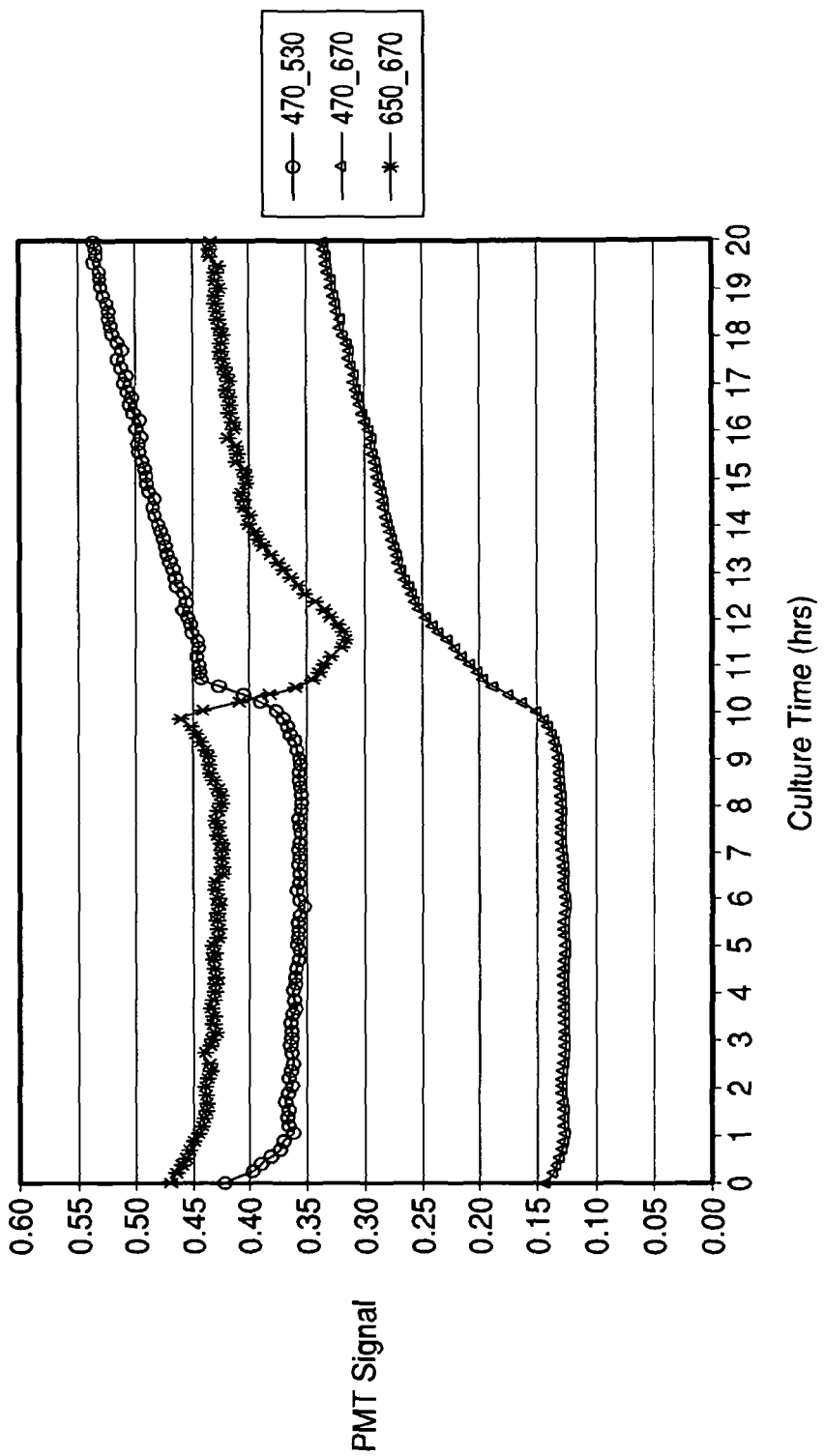

FIGS. 10A-10F shows the percent change in fluorescence signal over time at six selected wavelengths for eleven species of microorganisms. FIG. 10A shows data collected with an excitation wavelength of 300 nm and an emission wavelength of 490 nm for various species, FIG. 10B shows data collected with an excitation wavelength of 360 nm and an emission wavelength of 380 nm for various species, FIG. 10C shows data collected with an excitation wavelength of 460 nm and an emission wavelength of 480 nm for various species, FIG. 10D shows data collected with an excitation wavelength of 480 nm and an emission wavelength of 510 nm for various species, FIG. 10E shows data collected with an excitation wavelength of 520 nm and an emission wavelength of 740 nm for various species, and FIG. 10F shows data collected with an excitation wavelength of 610 nm and an emission wavelength of 640 nm for various species.

The measurements and data collected for characteristic fluorescence and/or diffuse reflectance patterns over time, and/or change in fluorescence signal over time at multiple wavelengths can be compared to a database of EEM and scattering data from known microorganism strains, and used to detect and characterize a biological particle that may be present in a sample.

FIGS. 11A-11D show the percentage of strains correctly identified to different classification models using general discriminant analyses of microbial group-specific temporal changes in fluorescence and/or diffuse reflectance data using a different numbers of data points in the model. Measurements taken for multiple data points from each sample tested were compared to a database of EEM and reflectance data from blood cultures of approximately 120 known microorganism strains, and each test strain was classified based on the comparisons. FIG. 11A shows classification by Clinical Gram group, and shows that approximately 93% of species tested were correctly identified to the Clinical Gram level 0-4 hours after detection based on 11 data points. FIG. 11B shows classification by Therapeutic Group level, and shows that approximately 97% of species tested were correctly characterized 0-4 hours after detection based on the same 11 data points. FIG. 11C shows classification by Therapeutic Group level, and shows that approximately 96% of species tested were correctly characterized 0-7 hours after detection based on the same 11 data points. FIG. 11D shows classification by Therapeutic Group, and shows that approximately 98% of species tested were correctly characterized 0-7 hours after detection based on a different input of 21 data points.

FIGS. 11A-11D demonstrate that analysis of microbial-specific changes in fluorescence can be used to classify microorganisms into clinically relevant groups or categories based on either existing nomenclature or the organism's innate metabolism, pathogenicity and virulence characteristics.

Example 7

Proof-of-Concept Blood Culture System Using Commercial Blood Culture Bottles A proof-of-concept blood culture system was developed to demonstrate the capabilities of the new technology in commercially manufactured BacT/ALERT® (bioMérieux, Inc.) culture bottles with and without the indwelling Liquid Emulsion Sensor (LES). This system was capable of testing one bottle at a time using the same temperature and agitation conditions as the commercial BacT/ALERT® Microbial Detection System (bioMérieux, Inc.).

Two light sources were used to generate the excitation light; one was a 470 nm laser and the other was a 650 nm laser. Coherent light sources were used so that an evaluation could be done with narrow Stokes shifts. It is also advantageous to use a coherent light source in a fiber optic application since the optical coupling efficiency is higher with a laser. Narrowband optical filters restrict fluorescence (or amplified spontaneous emission) from entering into the fiber; this ensures the fluorescence signal alone is from fluorophores of interest in the sample. The filtered light from each of the sources is coupled into the bifurcated fiber using fiber optic coupling optics (well known to those in the field). The birfurcated fiber combines the light of two fibers into one which is incident onto the sample bottle. A classical reflectance probe configuration (6 collection fibers around 1 excitation fiber was used). The collection fibers collect the reflected excitation light and the fluorescent light and couple it back to a bifurcating fiber (which splits the light into two paths). The light is then extracted from the fiber optics and collimated using a collimation optical assembly. Bandpass filters are used to separate the fluorescence from each channel so that one photodetection system detects the fluorescence from the 470 nm source and the other detects the fluorescence from the 650 nm source. Each of the filters blocks the excitation light frequency. A block diagram of the system is shown in FIG. 14.

Plastic BacT/ALERT® SA (bioMérieux, Inc.) culture bottles were filled with 10 mL of normal human blood or defibrinated horse blood and seeded with $10^2$-$10^3$ CFU of a variety of microorganisms. Bottles were loaded into the instrument and read every 10 minutes for up to 120 hours. The fiber optic probe was placed adjacent to the side-wall of the rocking culture bottle at angles between 0 and 90 degrees. Additionally, BacT/ALERT® SA bottles were made without the indwelling Liquid Emulsion Sensor (LES) and the fiber optic probe placed perpendicular to the bottom of the tube to collect data.

The results of several side-wall read cultures are shown in FIGS. 12A-12D for *S. pneumoniae, E. faecalis, P. mirabilis* and *C. hominis* respectively. Obvious changes in fluorescence intensity occurred due to microbial growth for both test wavelengths (Ex650/Em670 nm and Ex470/Em670 nm). Furthermore, the extent, rate and direction of the fluorescence signal differed between the species tested.

The results of several bottom-wall read cultures are shown in FIGS. 13A-13D for *S. pneumoniae, P. mirabilis, S. aureus* and *E. coli* respectively in BacT/ALERT® SA bottles made without the indwelling Liquid Emulsion Sensor (LES). Characteristic changes in fluorescence intensity, rate and direction were observed for these species of microorganisms within a few hours of initial detection.

FIGS. 12A-D and 13A-D demonstrate that analysis of microbial-specific changes in fluorescence can be used to classify microorganisms into clinically relevant groups or categories based on either existing nomenclature or the organism's innate metabolism, pathogenicity and virulence characteristics.

That which is claimed is:

1. A method for detecting and characterizing a microorganism present in a sample, said method comprising: combining said sample with a growth composition, obtaining at least two time-dependent measurements directly from said sample and growth composition, wherein said at least two time-dependent measurements comprise directly measuring intrinsic fluorescence from said sample and growth composition and correlating said measurements to detect and characterize any microorganism present in said sample.

2. The method according to claim 1 where said sample comprises blood, or bodily fluids.

3. The method according to claim 2 wherein said sample is a clinical sample and said growth composition is a liquid culture media.

4. The method according to claim 1 wherein said sample is a non-clinical sample.

5. The method according to claim 1 wherein said microorganism is characterized into on one or more classification models selected from the group consisting of Gram Groups, Clinical Gram Groups, Therapeutic Groups, Functional Groups, and Natural Intrinsic Fluorescence Groups.

6. The method according to claim 5 wherein said classification model characterizes said microorganism into a Gram Group selected from the group consisting of Gram positive microorganisms that stain dark blue with Gram stain, Gram negative microorganisms that stain red with Gram stain, or yeast cells that stain dark blue with Gram stain.

7. The method according to claim 5 wherein said classification model characterizes said microorganism into a Clinical Gram Group selected from one or more of the group consisting of cocci, diplococci, rods, or bacilli.

8. The method according to claim 5 wherein said classification model characterizes said microorganism into a Therapeutic Group wherein highly resistant enterobacteriacae (EB) species are distinguished from sensitive EB species, or fluconazole-resistant *candida* species are distinguished from sensitive *candida* species.

9. The method according to claim 1 wherein upon detection of said microorganism, an automated notification is provided.

10. The method according to claim 9 wherein said detection occurs less than 48 hours.

11. The method according to claim 1 wherein said intrinsic fluorescence comprises front-face fluorescence and wherein said at least two time-dependent measurements further comprises diffuse reflectance, and said composition comprises a liquid culture media.

12. The method according to claim 11 wherein the intrinsic fluorescence comprises exciting the sample at a time-interval of from about every five minutes to about every hour.

13. The method according to claim 12 wherein said characterization occurs within 8 hours post detection.

14. The method according to claim 1 wherein said correlation comprises a comparison of said at least two time-dependent measurements with control measurements taken for known microorganisms.

15. The method according to claim 1 wherein said correlation is to characterize said microorganism.

16. The method according to claim 1 wherein said correlation is to detect said microorganism.

17. The method according to claim 1, wherein said microorganism is characterized to the genus level.

18. The method according to claim 1, wherein said microorganism is characterized to the species level.

\* \* \* \* \*